(12) United States Patent
Richards et al.

(10) Patent No.: US 7,396,508 B1
(45) Date of Patent: Jul. 8, 2008

(54) AUTOMATED MOLECULAR PATHOLOGY APPARATUS HAVING INDEPENDENT SLIDE HEATERS

(75) Inventors: William Richards, Tucson, AZ (US); Charles D. Lemme, Tucson, AZ (US); Kimberly Christensen, Tucson, AZ (US); Ethel R. Macrea, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 09/614,401

(22) Filed: Jul. 12, 2000

(51) Int. Cl.
*G01N 31/00* (2006.01)
*G01N 1/10* (2006.01)
*G01N 35/02* (2006.01)
*G01N 35/10* (2006.01)
*B01L 3/02* (2006.01)

(52) U.S. Cl. .................. 422/64; 422/100; 422/63; 422/67; 422/68.1; 422/104; 141/145; 436/43; 436/45; 436/180; 219/385

(58) Field of Classification Search .............. 422/104, 422/100, 67, 63–64, 68.1; 141/145; 436/180, 436/43, 45; 219/385
See application file for complete search history.

(56) References Cited

U.S. PATENT DOCUMENTS

| | | | |
|---|---|---|---|
| 3,911,749 A | | 10/1975 | Hendry |
| 4,043,292 A | * | 8/1977 | Rogers et al. .............. 118/5 |
| 4,181,850 A | * | 1/1980 | Fairbairn ................. 250/445 T |
| 4,219,529 A | * | 8/1980 | Tersteeg et al. ............... 422/64 |
| 4,234,539 A | * | 11/1980 | Ginsberg et al. ............... 422/64 |
| 4,283,901 A | * | 8/1981 | Schieser et al. ............... 53/272 |
| 4,303,611 A | * | 12/1981 | Jessop ..................... 422/65 |
| 4,430,299 A | * | 2/1984 | Horne ..................... 356/246 |
| 4,573,001 A | * | 2/1986 | Lin ....................... 318/695 |
| 4,721,680 A | | 1/1988 | Jeffs et al. |
| 4,858,155 A | * | 8/1989 | Okawa et al. ............... 364/557 |
| 4,865,986 A | * | 9/1989 | Coy et al. ................. 435/290 |
| 4,888,998 A | | 12/1989 | Buzza et al. |
| 4,962,041 A | | 10/1990 | Roginski et al. |
| 4,974,459 A | | 12/1990 | Maekelae et al. |
| 4,993,593 A | * | 2/1991 | Fabiano et al. ............... 222/1 |
| 5,071,625 A | * | 12/1991 | Kelln et al. ................. 422/72 |
| 5,075,079 A | * | 12/1991 | Kerr et al. .................. 422/64 |
| 5,081,872 A | | 1/1992 | Greter et al. |
| 5,089,229 A | * | 2/1992 | Heidt et al. ................. 422/63 |

(Continued)

FOREIGN PATENT DOCUMENTS

DE 324481 6/1983

(Continued)

OTHER PUBLICATIONS

Nuovo, "In Situ PCR: Protocols and Applications", PCR Methods and Applications, pp. 151-167 (1995).

*Primary Examiner*—Brian R. Gordon
(74) *Attorney, Agent, or Firm*—McDonnell Boehnen Hulbert & Berghoff LLP

(57) ABSTRACT

Apparatus and methods for automatically staining or treating multiple tissue samples mounted on microscope slides are provided. Individualized slide temperature control is accomplished by the heating system according to the present invention that has thermal platforms radially mounted to the carousel for heating the slides and sensing the temperature of each. The heating system also permits automated de-waxing if necessary.

11 Claims, 22 Drawing Sheets

U.S. PATENT DOCUMENTS

| | | | | |
|---|---|---|---|---|
| 5,250,262 A * | 10/1993 | Heidt et al. | | 422/63 |
| 5,264,182 A | 11/1993 | Sakagami et al. | | |
| 5,273,588 A * | 12/1993 | Foster et al. | | 118/715 |
| 5,273,905 A | 12/1993 | Muller et al. | | |
| 5,336,467 A * | 8/1994 | Heidt et al. | | 422/64 |
| 5,439,649 A | 8/1995 | Tseung et al. | | |
| 5,538,871 A | 7/1996 | Nuovo et al. | | |
| 5,595,707 A * | 1/1997 | Copeland et al. | | 422/64 |
| 5,597,733 A | 1/1997 | Bell et al. | | |
| 5,601,141 A | 2/1997 | Gordon et al. | | |
| 5,645,114 A * | 7/1997 | Bogen et al. | | 141/145 |
| 5,654,199 A | 8/1997 | Copeland et al. | | |
| 5,654,200 A * | 8/1997 | Copeland et al. | | 422/100 |
| 5,697,409 A * | 12/1997 | Bishop et al. | | 141/284 |
| 5,758,073 A * | 5/1998 | Liang et al. | | 395/200.6 |
| 5,819,842 A * | 10/1998 | Potter et al. | | 165/206 |
| 5,844,342 A * | 12/1998 | Miyatani et al. | | 310/112 |
| 5,881,781 A * | 3/1999 | Bishop | | 141/284 |
| 5,925,135 A * | 7/1999 | Trieu et al. | | 713/400 |
| 5,948,271 A * | 9/1999 | Wardwell et al. | | 210/143 |
| 6,016,959 A * | 1/2000 | Kamo et al. | | 235/449 |
| 6,061,925 A * | 5/2000 | Amano et al. | | 34/141 |
| 6,063,589 A * | 5/2000 | Kellogg et al. | | 435/24 |
| 6,096,271 A * | 8/2000 | Bogen et al. | | 422/64 |
| 6,180,061 B1 | 1/2001 | Bogen et al. | | |
| 6,183,693 B1 * | 2/2001 | Bogen et al. | | 422/64 |
| 6,216,547 B1 * | 4/2001 | Lehtovaara | | 73/862.391 |
| 6,245,680 B1 * | 6/2001 | Shendon et al. | | 438/692 |
| 6,249,338 B1 * | 6/2001 | Ohtomo et al. | | 356/139.07 |
| 6,277,265 B1 * | 8/2001 | Hanak | | 205/687 |
| 6,296,610 B1 * | 10/2001 | Schneider et al. | | 600/445 |
| 6,296,809 B1 | 10/2001 | Richards et al. | | |
| 6,593,143 B1 * | 7/2003 | Gordon | | 436/45 |
| 6,605,474 B1 * | 8/2003 | Cole | | 436/177 |
| 6,706,519 B1 * | 3/2004 | Kellogg et al. | | 435/287.2 |
| 2001/0045785 A1 * | 11/2001 | Chen et al. | | 310/104 |
| 2002/0026839 A1 * | 3/2002 | Lehtovaara | | 73/862.637 |
| 2002/0182113 A1 * | 12/2002 | Shvets et al. | | 422/99 |

FOREIGN PATENT DOCUMENTS

| | | |
|---|---|---|
| EP | 0360487 | 3/1990 |
| EP | 0602802 | 6/1994 |
| EP | 0701865 | 3/1996 |

* cited by examiner

AUTOMATED MOLECULAR PATHOLOGY APPARATUS HAVING INDEPENDENT SLIDE HEATERS

CROSS-REFERENCE APPLICATIONS

This is a continuation-in part of U.S. application Ser. No. 60/076,198 filed on Feb. 27, 1998, the subject matter of which is hereby incorporated herein.

FIELD OF THE INVENTION

The present invention is directed to apparatus for use in diagnostic molecular pathology and, more particularly, to such apparatus used for the automated staining and/or treating of tissue samples mounted on microscope slides.

BACKGROUND OF THE INVENTION

Molecular pathology is the examination at a molecular level of the DNA, MRNA, and proteins that cause or are otherwise associated with disease. From this examination important information about patient diagnosis, prognosis, and treatment options can be elucidated. The practice of molecular pathology is generally divided into two main areas: (i) analysis of DNA, mRNA, and proteins in intact cells (in-situ), and (ii) analysis of these biological materials after they have been extracted from tissues. The first category, to which the present invention is primarily directed, has the advantage that it allows the pathologist or scientist to study the histopathologic architecture or morphology of the tissue specimen under the microscope at the same time that the nucleic acid or proteins are being assayed. These techniques include immunohistochemistry (IHC) which looks at proteins, in-situ hybridization (ISH) which looks at nucleic acids, histochemistry (HC) which looks at carbohydrates, and enzyme histochemistry (EHC) which looks at enzyme chemistry. For example, ISH can be used to look for the presence of a genetic abnormality or condition such as amplification of cancer causing genes specifically in cells that, when viewed under a microscope, morphologically appear to be malignant. ISH is also useful in the diagnosis of infectious diseases as it allows detection not only of a microbial sequence but also of precisely which cells are infected. This may have important clinicopathologic implications and is an effective means to rule out the possibility that positive hybridization signal may have come from an adjacent tissue of no clinical concern or from blood or outside contamination.

IHC utilizes antibodies which bind specifically with unique epitopes present only in certain types of diseased cellular tissue. IHC requires a series of treatment steps conducted on a tissue section or cells (e.g. blood or bone marrow) mounted on a glass slide to highlight by selective staining certain morphological indicators of disease states. Typical steps include pretreatment of the tissue section to remove the paraffin and reduce non-specific binding, retrieval of antigens masked by cross-linking of the proteins from the chemical fixatives, antibody treatment and incubation, enzyme labeled secondary antibody treatment and incubation, substrate reaction with the enzyme to produce a fluorophore or chromophore highlighting areas of the tissue section having epitopes binding with the antibody, counterstaining, and the like. Most of these steps are separated by multiple rinse steps to remove unreacted residual reagent from the prior step. Incubations can be conducted at elevated temperatures, usually around 37° C., and the tissue must be continuously protected from dehydration. ISH analysis, which relies upon the specific binding affinity of probes with unique or repetitive nucleotide sequences from the cells of tissue samples or bodily fluids, requires a similar series of process steps with many different reagents and is further complicated by varying temperature requirements.

In view of the large number of repetitive treatment steps needed for both IHC and ISH, automated systems have been introduced to reduce human labor and the costs and error rate associated therewith, and to introduce uniformity. Examples of automated systems that have been successfully employed include the NEXES® and Gen II® staining Systems available from Ventana Medical Systems (Tucson, Ariz.) as well as the system disclosed in U.S. Pat. No. 5,654,199 to Copeland et al. These systems employ a microprocessor controlled system including a revolving carousel supporting radially positioned slides. A stepper motor rotates the carousel placing each slide under one of a series of reagent dispensers positioned above the slides. Bar codes on the slides and reagent dispensers permits the computer controlled positioning of the dispensers and slides so that different reagent treatments can be performed for each of the various tissue samples by appropriate programming of the computer.

The aforementioned staining systems include either a hot air blower or a heat lamp to warm the samples above laboratory ambient temperatures for steps requiring elevated temperatures. Heating the slide improves staining quality by acceleration of the chemical reaction and can permit a reaction temperature more closely matching body temperature (about 37° C.) at which antibodies are designed to react. While such convection or radiant heating systems have been generally suitable for IHC, which is antibody based, they are less suitable for ISH, which is nucleic acid based and requires higher and more precise temperature control. In order to denature the DNA double helix of both the target sample and the probe so as to render them single stranded, the temperature must be raised above the melting point of the duplex, usually about 94° C. At the same time it is imperative that the sample not be overheated past 100° C. as doing so destroys cell morphology making it difficult to view under a microscope. Precise temperature control is also required in ISH to effect probe hybridization at the desired stringency. The selected temperature must be low enough to enable hybridization between probe and template, but high enough to prevent mismatched hybrids from forming. It would be desirable, therefore, to have an automatic tissue staining apparatus which can control the temperature of reactions with enough precision for most ISH applications.

Another disadvantage of the heating units typically employed with automated tissue stainers is that they do not permit the temperature of individual slides to be separately controlled. With prior art systems all of the slides are heated to the same temperature at any given time during the process. For example, U.S. Pat. No. 5,645,114 to Bogen et al. discloses a dispensing assembly adapted to carry a plurality of microscope slides. Individual slide holders containing resistive heating imits are provided. However, with the assembly taught by Bogen et al., all of the slides would be heated to a common temperature because, for example, no means are disclosed for separate heating controls or for shielding slides from heat generated by adjacent slides. This precludes protocols having different temperature parameters from being run on different samples at the same time. For example, DNA probe assays having different stringency requirements could not be run efficiently at the same time. It would be desirable, therefore, to have an automatic tissue staining apparatus wherein adjacent slides can have different tests applied to them even when the tests have unique heating requirements.

A difficulty frequently encountered in both IHC and ISH testing results from the manner in which the tissues are typically preserved. The mainstay of the diagnostic pathology laboratory has been for many decades the formalin-fixed, paraffin embedded block of tissue, sectioned and mounted upon glass slides. Fixation in such a preservative causes cross-linking of macromolecules, both amino acids and nucleic acids. These cross-linked components must be removed to allow access of the probe to the target nucleic acid and to allow the antibody to recognize the corresponding antigen. "Unmasking" the antigen and/or nucleic acid is typically accomplished manually with multiple pretreatment, protolytic digestion, and wash steps. It would be desirable if the process of conditioning cells so that their antigens and nucleic acids are available for detection could be automated.

Prior to staining, complete removal of the paraffin is also required so that it does not interfere with antibody or probe binding. Paraffin, a hydrophobic substance, must be removed prior to staining or hybridization using probes. Deparaffinization is normally achieved by the use of two or three successive clearing reagents that are paraffin solvents such as xylene, xylene substitutes or toluene which may be toxic, flammable and pose environmental hazards. Safer and faster methods to deparaffinize the slides would be advantageous.

SUMMARY OF THE INVENTION

The present invention is directed to apparatus and methods for automatically staining or treating multiple tissue samples mounted on microscope slides so that each sample can receive an individualized staining or treatment protocol even when such protocols require different temperature parameters. Thus, different DNA probe and/or antibody based staining procedures can be nm simultaneously despite the fact that each may have different heating requirements at a given point in time. Additionally, samples requiring de-waxing (e.g. tumor sections) can be automatically processed at the same time as other samples (e.g. smears) that do not require this preliminary step.

More specifically, the apparatus is a computer controlled, bar code driven, staining instrument that automatically applies chemical and biological reagents to tissue or cells mounted or affixed to standard glass microscope slides. Up to 20 slides are mounted in a circular array to a carousel which rotates, as directed by the computer, placing each slide under one of a series of reagent dispensers positioned above the slides. Each slide receives the selected reagents (e.g. DNA probe) and is washed, mixed and/or heated in an optimum sequence and for the required period of time. Tissue sections so stained or treated are then removed from the apparatus by the user to be viewed under a microscope by a medical practitioner who reads the slide for purposes of patient diagnosis, prognosis, or treatment selection. The computer controlled automation permits use of the apparatus in a "walk-away" manner, i.e. with little manual labor.

Individualized slide temperature control is accomplished by the heating system according to the present invention that has thermal platforms radially mounted to the carousel for heating the slides and sensing the temperature of each. A printed circuit board, also mounted to the slide carousel, individually monitors and controls each thermal platform separately. Information and power pass between the rotating carousel and the fixed apparatus via a slip ring assembly. This information includes the upper and lower temperature parameters needed for heating each of the 20 slides for the appropriate time period.

A key advantage of the present invention is that each sample can receive an individualized staining or treatment protocol even when such protocols require different—temperature parameters.

Another advantage of the present invention is that it allows the temperature of the entire surface of the slide to which the tissue is mounted to be carefully controlled (i.e. within plus or minus two degrees Celsius of the desired temperature). Such precision is particularly necessary for DNA denaturation and probe hybridization in ISH and related processes such as in-situ PCR. Furthermore, since the heating according to the present invention is made uniform, this narrow temperature range is maintained throughout the surface of the slide so that the tissue is evenly heated regardless of its position on the slide.

Still another advantage of the present invention is that it permits the de-waxing of the tissue sample in an automated foHnat without reliance upon harmful solvents such as xylene.

Yet another advantage of the present invention is that by heating the tissue in an aqueous solution the tissue is better conditioned for staining by rendering the targeted molecules in the cells more accessible to the stain.

Still another advantage of the present invention is its ability to rapidly heat the surface of the slide to which the tissue is mounted (i.e. from 37° C. to 95° C. in under two minutes and to cool down over same range in under four minutes) so as to permit DNA denaturation without over-denaturation and loss of cell morphology due to excess heating.

Yet another advantage of the present invention is its ability to dehydrate the tissue sample following staining using heat.

Still another advantage of the present invention is the negation of human error and increase in productivity resulting from automation.

With the foregoing and other objects, advantages and features of the invention that will become hereinafter apparent, the nature of the invention may be more clearly understood by reference to the following detailed description of the invention, the appended claims and to the several views illustrated in the drawings.

DETAILED DESCRIPTION OF THE INVENTION

Figure 1:
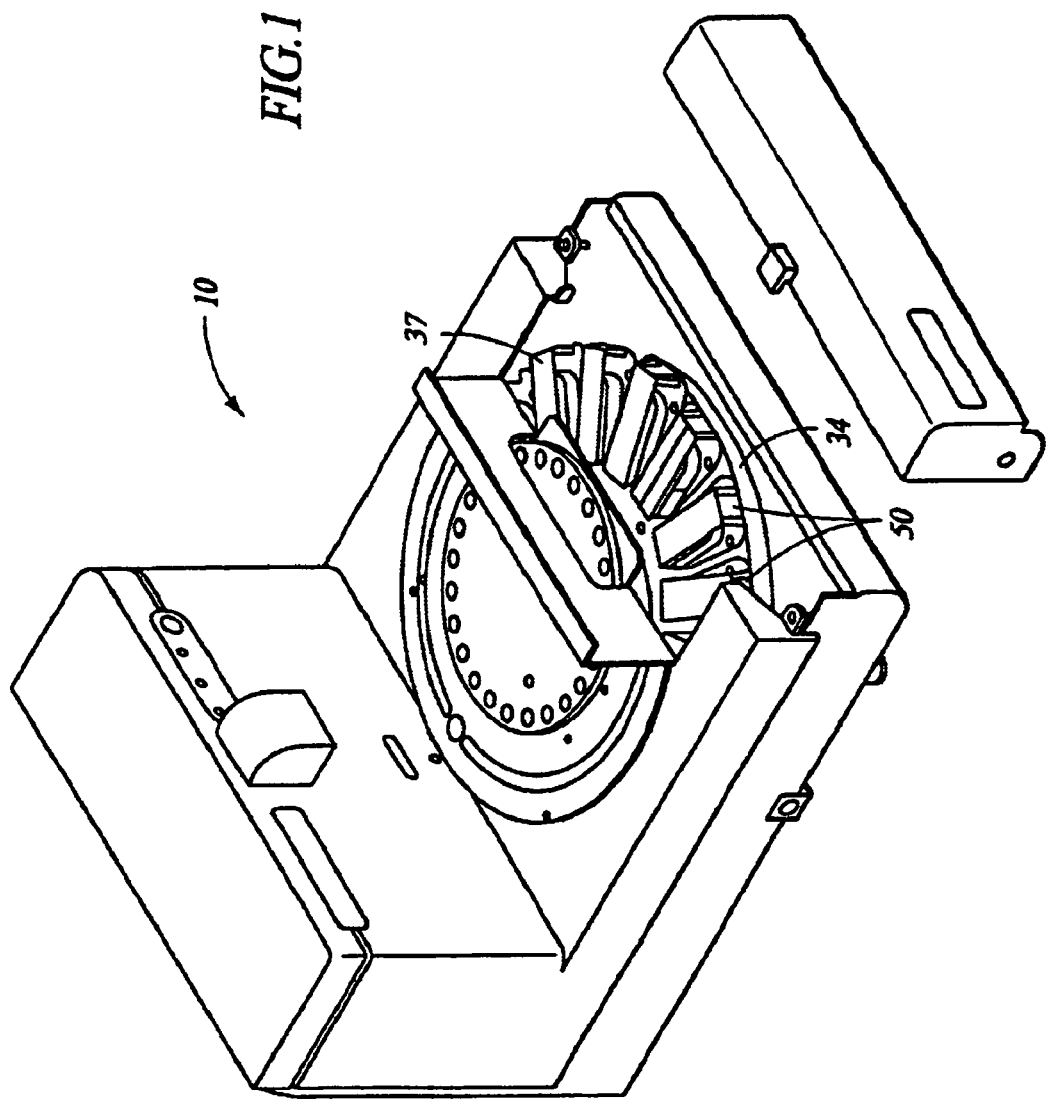
FIG. 1 is a perspective view of the present invention shown with the slide hood open and the carousel door removed.

Referring now in detail to the drawings wherein like parts are designated by like reference numerals throughout, there is illustrated in FIG. 1 a perspective view of the molecular pathology apparatus according to the present invention which is designated generally by reference numeral 10. Apparatus 10 is designed to automatically stain or otherwise treat tissue mounted on microscope slides with nucleic acid probes, antibodies, and/or reagents associated therewith in the desired sequence, time and temperature. Tissue sections so stained or treated are then to be viewed under a microscope by a medical practitioner who reads the slide for purposes of patient diagnosis, prognosis, or treatment selection.

Figure 2:
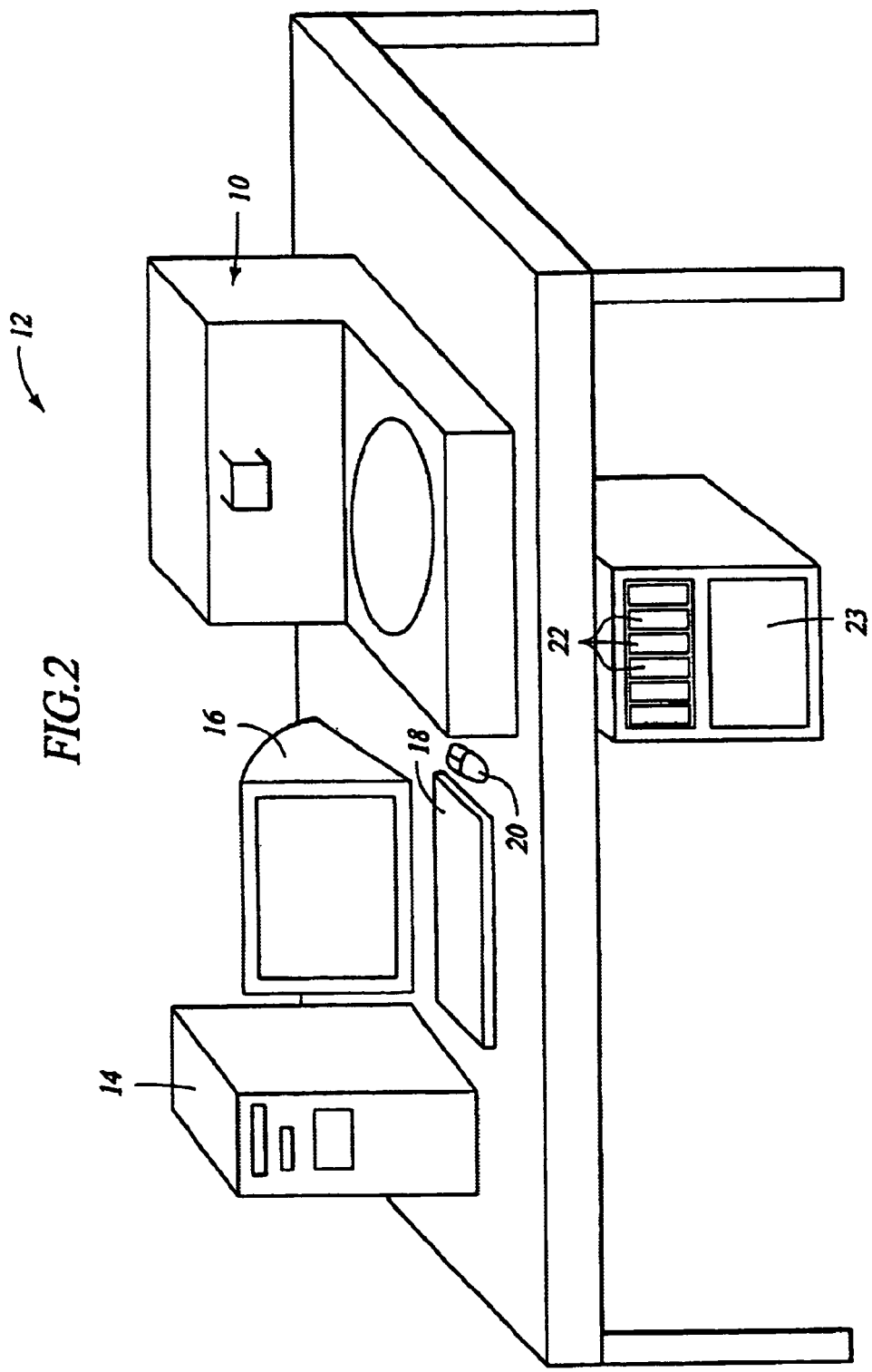
FIG. 2 is a perspective view of the present invention shown in conjunction with a computer and other instruments with which it operates.

In a preferred embodiment, apparatus 10 functions as one component or module of a system 12 (FIG. 2) which also comprises a host computer 14 preferably a personal computer, monitor 16, keyboard 18, mouse 20, bulk fluid containers 22, waste container 23 and related equipment. Additional staining modules or other instruments may be added to system 12 to form a network with computer 14 functioning as a server. Alternatively, some or all of these separate components could be incorporated into apparatus 10 making it a stand-alone instrument.

The preferred configuration of apparatus 10 as well as system 12 is generally as described in U.S. patent application Ser. No. 08/995,052 filed Dec. 19, 1997 as well as in the *Ventana NexES User's Guide* available from Ventana Medical Systems, Inc. (Tuscon, Ariz.), both incorporated herein, except with respect to the novel heating system, slide support, bulk fluids module, volume adjust, and slide wipe as disclosed below. For purposes of clarity, detailed descriptions of those components found in both the present invention and the incorporated references are omitted.

In brief, apparatus 10 is a microprocessor controlled staining instrument that automatically applies chemical and biological reagents to tissue mounted on standard glass microscope slides. A carousel supporting radially positioned glass slides is revolved by a stepper motor to place each slide under one of a series of reagent dispensers. Apparatus 10 controls dispensing, washing, mixing, and heating to optimize reaction kinetics. The computer controlled automation permits use of apparatus 10 in a walk-away manner, i.e. with little manual labor.

More particularly, apparatus 10 comprises a housing formed of a lower section 30 removably mounted or hinged to an upper section 32. A slide carousel 34 is mounted in lower section 30 for rotation about axis A-A. As set forth in greater detail below, a plurality of thermal platforms 50 are mounted radially about the perimeter of carousel 34 upon which standard glass slides with tissue samples may be placed. Carousel 34 is preferably constructed of stainless steel. It is a key feature of the present invention that the temperature of each slide may be individually controlled by means of various sensors and microprocessors as described herein. Also housed within apparatus 10 (FIG. 3) are wash dispense nozzles 36, Coverslip™ dispense nozzle 37, fluid knife 38, wash volume adjust nozzle 39, bar code reader mirror 40, and air vortex mixers 42 the details of which are discussed hereinafter.

Figure 4:
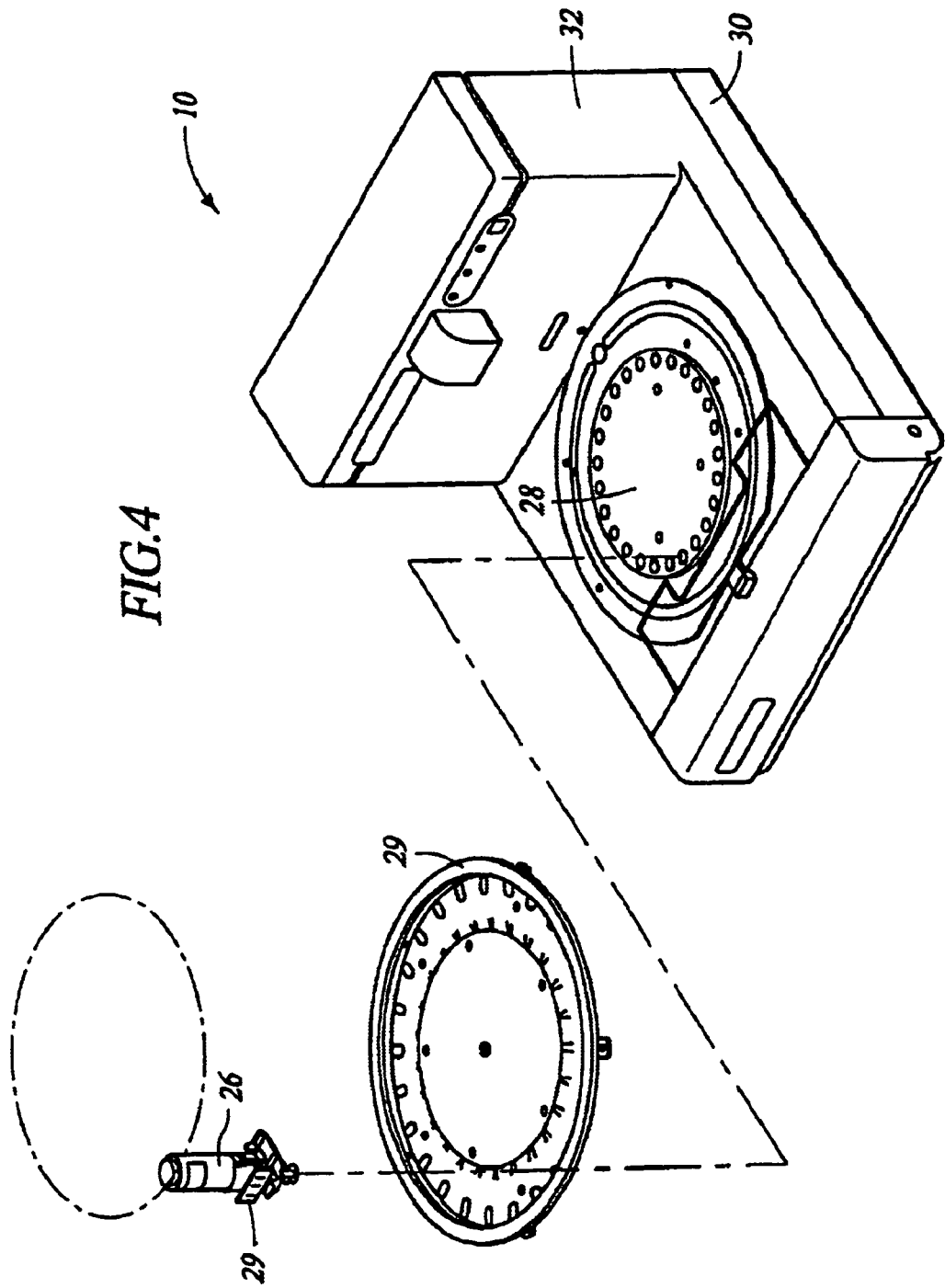
FIG. 4 is a perspective view of the present invention shown with a reagent dispenser.

Rotatably mounted atop upper section 32 is a reagent carousel 28. Dispensers 26 are removably mounted to reagent tray 29 (FIG. 4) which, in turn, is adapted to engage carousel 28. Reagents may include any chemical or biological material conventionally applied to slides including nucleic acid probes or primers, polymerase, primary and secondary antibodies, digestion enzymes, pre-fixatives, post-fixatives, readout chemistry, and counterstains. Reagent dispensers 26 are preferably bar code labeled 29 for identification by the computer. For each slide, a single reagent is applied and then incubated for a precise period of time in a temperature-controlled environment. Mixing of the reagents is accomplished by compressed air jets 42 aimed along the edge of the slide thus causing rotation of the reagent. After the appropriate incubation, the reagent is washed off the slide using nozzles 36. Then the remaining wash buffer volume is adjusted using the volume adjust nozzle 39. Coverslip™ solution, to inhibit evaporation, is then applied to the slide via nozzle 37. Air knife 38 divides the pool of Coverslip™ followed by the application of the next reagent. These steps are repeated as the carousels turn until the protocol is completed.

In addition to host computer 14, apparatus 10 preferably includes its own microprocessor 44 to which information from host computer 14 is downloaded. In particular, the computer downloads to microprocessor 44 both the sequence of steps in a run program and the sensor monitoring and control logic called the "run rules" as well as the temperature parameters of the protocol. Model No. DS225 IT 128K. from Dallas Semiconductor, Dallas Tex. is an example of a microprocessor that can perform this function.

Figure 5:
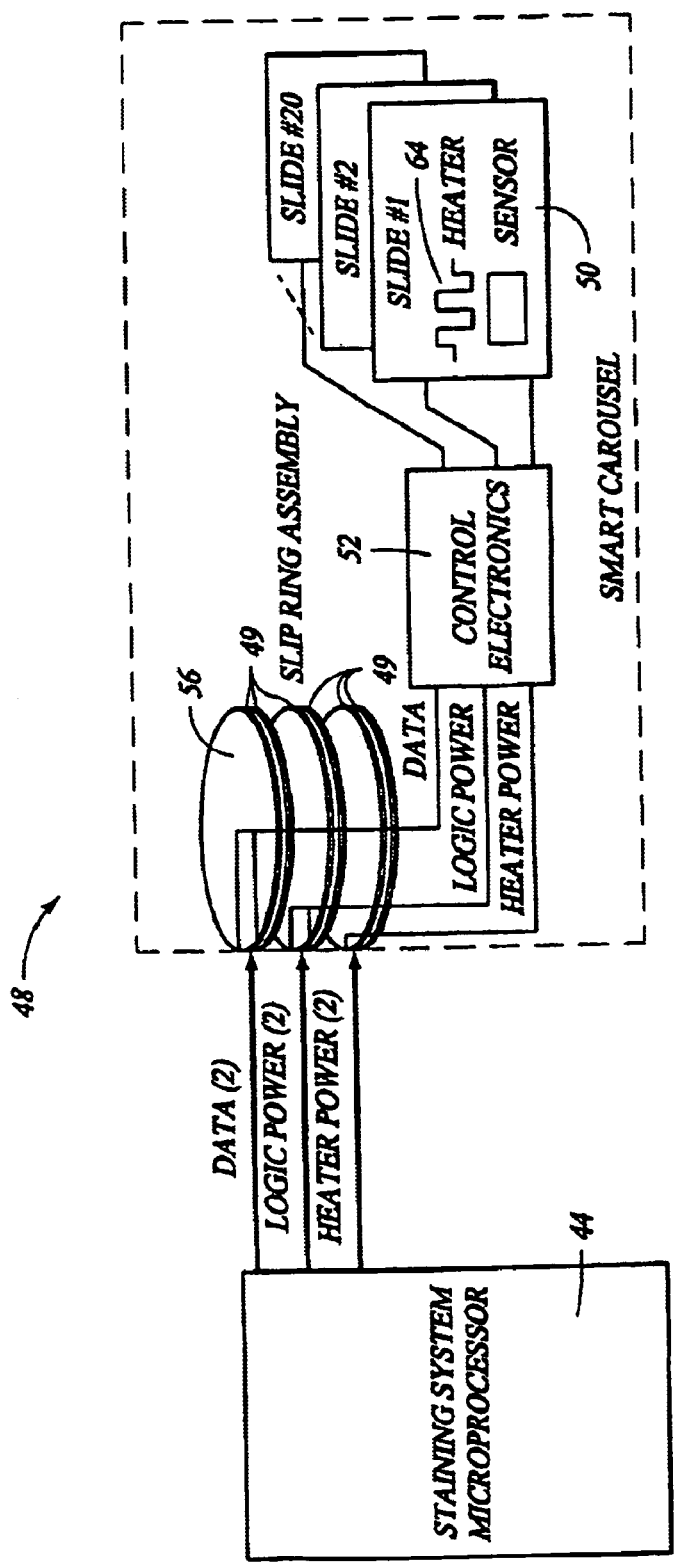
FIG. 5 is a block diagram of the heating system of the present invention.
Figure 6:
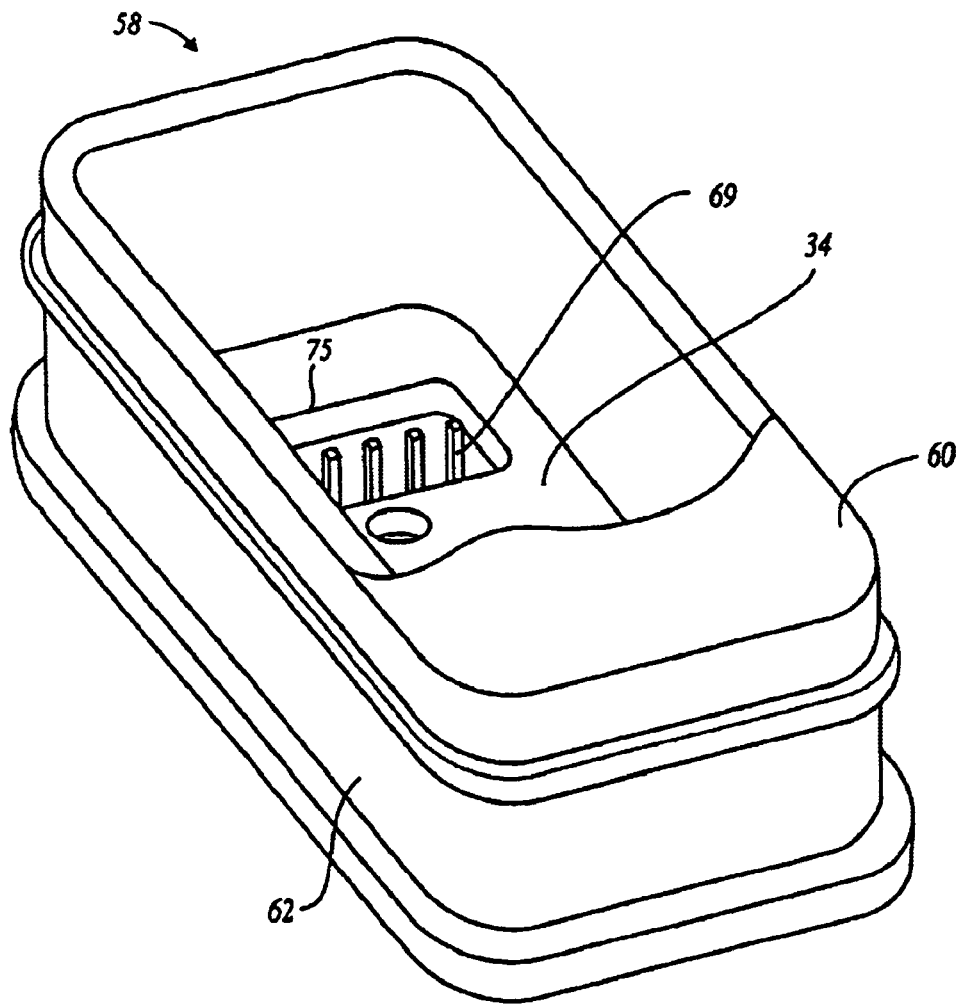
FIG. 6 is a perspective view of the heater/sensor unit of the present invention shown with the plate partially broken away to reveal the pins which are part of the control electronics.

Turning now to FIG. 5 there is shown a block diagram of the slide heating system 48. The system generally comprises about twenty thermal platforms 50, radially mounted to carousel 34, for heating the slides and monitoring the temperature thereof, and control electronics printed circuit board 52 also mounted to the slide carousel for monitoring the sensors and controlling the heaters. Control electronics 52 are mounted under the rotating slide carousel 34. Information and power are transferred from the fixed instrument platform to the rotating carousel via a slip ring assembly 56. This information includes the temperature parameters needed for heating the slides (upper and lower) communicated from microprocessor 44 (after having been downloaded from computer 14) to control electronics 52 as described below. If, during a run, the slide temperature is determined to be below the programmed lower limit, the thermal platform heats the slide. Likewise, if the slide temperature is found to be above the upper limit, heating is stopped. (See Block 88 of FIG. 14). A power supply of sufficient capacity to provide about eight watts per heater is provided to meet the requisite rate of temperature rise (a/k/a "ramp up").

Similarly, in an alternate embodiment, the cooling of the slides may be likewise controlled, as described subsequently. In one alternate embodiment, cooling platforms are mounted below the slide. The cooling platforms may comprise Peltier-type thermal transducers. In an alternative embodiment, a cooling device such as a fan (not shown) may optionally be provided if rapid cooling of the slides is required for particular applications. The cooling device will modify the ambient air for all of the platforms, necessitating the heaters corresponding to the slides which should not be cooled to compensate for the drop in ambient air temperature.

The slide heating system described herein uses conduction heating and heats slides individually. The system provides more accurate on-slide temperature and allows for temperature settings on a slide by slide basis. Each of the components of heating system 48 are now described in more detail.

Thermal Platforms

With reference to FIGS. 6-10 thermal platforms 50 comprises two components: a heater/sensor unit 58 and a housing 70 for removably mounting heater/sensor unit 58 to carousel 34 and for supporting the slides 37.

Heater/sensor unit 58 has a plate 60, about two inches long and one inch wide, preferably constructed of .04 inch thick brass plate. In lieu of brass, another material may be employed if it is both rigid and has sufficient conductivity to dissipate heat evenly throughout its surface so that the slide is warmed in a uniform manner. The plate may optionally be covered with a corrosion resistant material such as Teflon®.

It is a particular feature of the present invention that adjacent slides may optionally be heated to different temperatures at particular points in time. This is accomplished by making the slides thermally isolated from one another by having high thermal resistance between the heaters. As one skilled in the art will readily appreciate, thermal resistance is a function of the conductivity of the material, the thickness of the material, and the distance the heat must travel. Hence, a variety of materials may be employed to thermally isolate adjacent slides including rubber, plastics, ceramics, or metals if they provide thermal resistance based on the aforementioned criteria. As used herein, the term "thermally isolated" means that the heat from one heater has no appreciable affect on the temperature of adjacent slides. In addition, a variety of structures may be employed to thermally isolate adjacent slides including mounting the slide on a thermally resistant material, mounting a thermally resistant material in between slides, and placing the slides on a thermally resistant platform.

In a preferred embodiment, mounted about the perimeter of plate 60 and depending perpendicularly from the underside thereof is a skirt 62 preferably constructed of rubber or a similar material that is both waterproof and a thermal insulator. The insulative properties of skirt 62 helps to facilitate these temperature differentials between adjacent slides. It should be appreciated that a variety of materials may be employed in lieu of rubber to thermally insulate adjacent slides including ceramics and plastics that can withstand temperatures of at least 100° C. Also, the components housed within the cavity of heater/sensor unit 58 (to be described) must be shielded from the various heated solutions (oil and water based) that will be applied during the staining operation of the apparatus. Hence, plate 60 is preferably bonded to skirt 62 through vulcanizing or a similar process that results in a fluid impervious seal even at high temperatures. The walls of skirt 62 must be similarly resistant to such heated solutions. In a preferred embodiment, the thickness of the skirt 62 is 0.06 inch for rubber material, thereby minimizing the cross sectional area through which heat may travel. Alternatively, skirt 62 may be constructed of a metallic material, such as brass, sufficiently thin (e.g., approximately 0.01 inch) to provide thermal resistance. When mounted to carousel 34 the height of skirt 62 is about one-half inch thereby elevating plate 60 and the slide supported thereon by that same distance. Elevating the platform upon which the slides are placed distances them from the various fluids that collect on the carousel 34 during operation and thermally isolate or insulate the slides from heat generated . by adjacent heaters.

Figure 7:
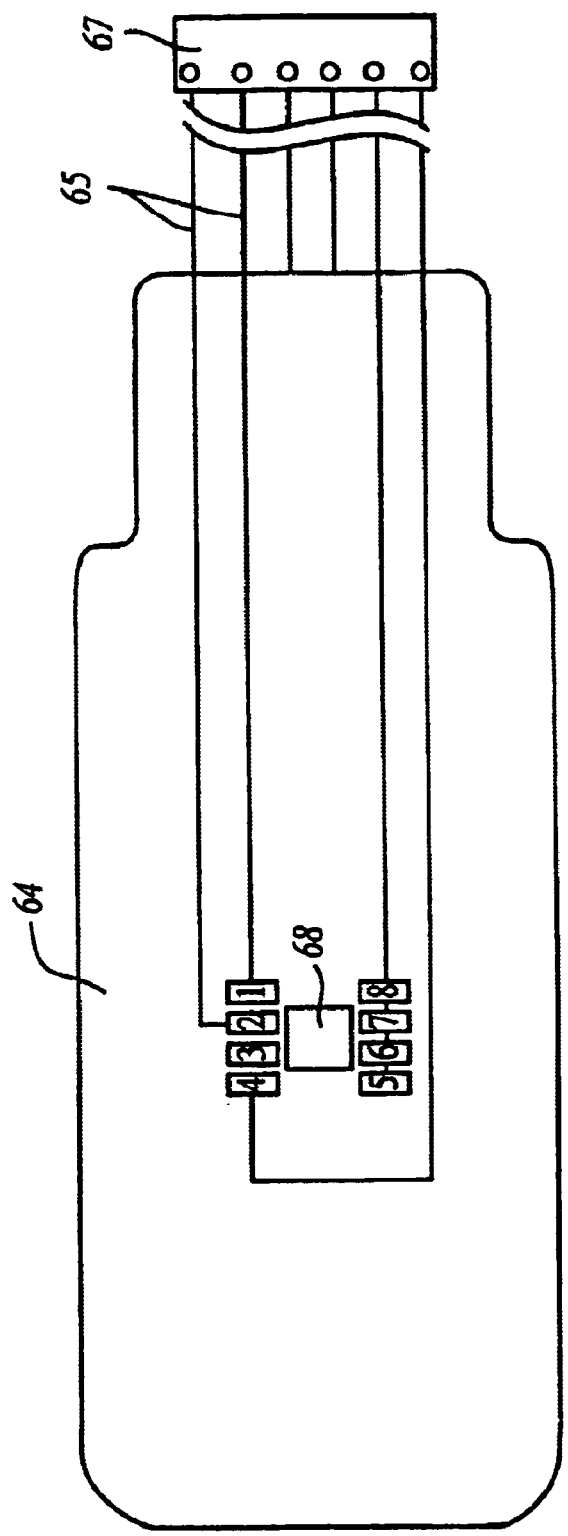
FIG. 7 is a plan view of a heater.
Figure 8:
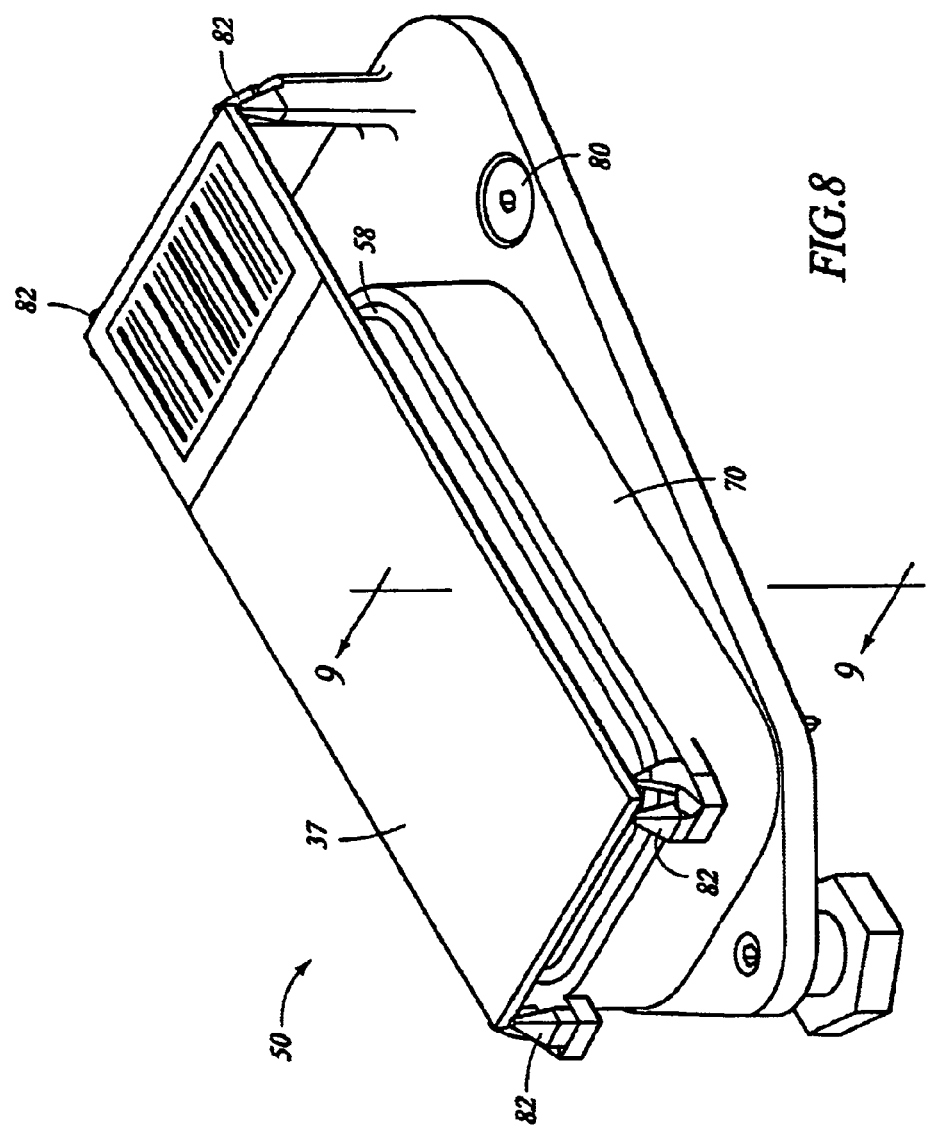
FIG. 8 is a perspective view of a thermal platform shown with a glass slide thereon.

A photo-etched resistive heater 64 is mounted to the underside of plate 60 within the cavity defined by skirt 62. The heater can be made of a variety of materials from high resistance, nickel based materials, such as Inconel, to more conductive materials, such as cuppro-nickel. Cuppro-nickel is preferred. The photo-etched resistor 64 is bonded to and retained between two, thin sheets of plastic such 0.008 inch thick Kapton"' polyimid film available from DuPont. Electrical leads 65 are welded to the ends of the resistive traces and these leads are brought out from between the two K.apton' layers and connected to the photo-etched resistor. One outer side of this sandwich is designated to be bonded to the heater while the other outer side has another, photo-etched circuit attached to it. The second circuit is for temperature sensing and has four low resistance traces which terminate in the center of the heater at solder pads which connect to a sensor made by Dallas Semiconductor, their part number DS 1721 S. The four traces are welded to four wires which exit in the same area as the wires connected to the heating traces. A third layer of Kapton™ is bonded over the control traces and this third layer has cutouts over the solder pads in the center so that the sensor can be attached. Six wires exit the heater, two for powering the heater and four for sensing the temperature, as shown in FIG. 7. The six wires are attached to a female, six circuit plug 67 which could be made by a number of companies, such as AMP (Harrisburg, Pa.) or Molex (Lisle, Ill.). The female connector slides over six, mating pins 69 that are soldered onto the control electronics circular PC board 52 described elsewhere. The PC board 52 is mounted under the slide carousel 34 opposite the side upon which the slide heaters are attached, so the six pins extend upward through a rectangular aperture 75 in the carousel.

A manufacturing source for heaters 64 according to the specifications set forth herein is Minco Products (Minneapolis, Minn.). As set forth in more detail below, heaters may be individually controlled by an integrated circuit driver or individual transistors (mounted to printed circuit board 52) capable of switching the heater current on and off.

The heater/sensor unit as described has the ability to rapidly heat the useful area of the slide from 37° C. to 95° C. in under two minutes and to cool down over same range in under four minutes so as to permit DNA denaturation without over-denaturation and loss of cell morphology due to excess heating.

Heating the slide surface uniformly is another key goal of the present invention since tissue specimens are often mounted in different positions on the slide. This poses a challenge for conduction heating, even when done manually, since traditional hot plates often generate patchy "hotspots" making it hard to know where to place the slide on the plate. If the cells throughout the tissue are not heated evenly, the microscope slide cannot be accurately interpreted. For example, if the temperature is not high enough to denature the probe and tissue DNA this may lead to false negatives and inconsistencies during stringency washes could lead to false positives.

Figure 12:
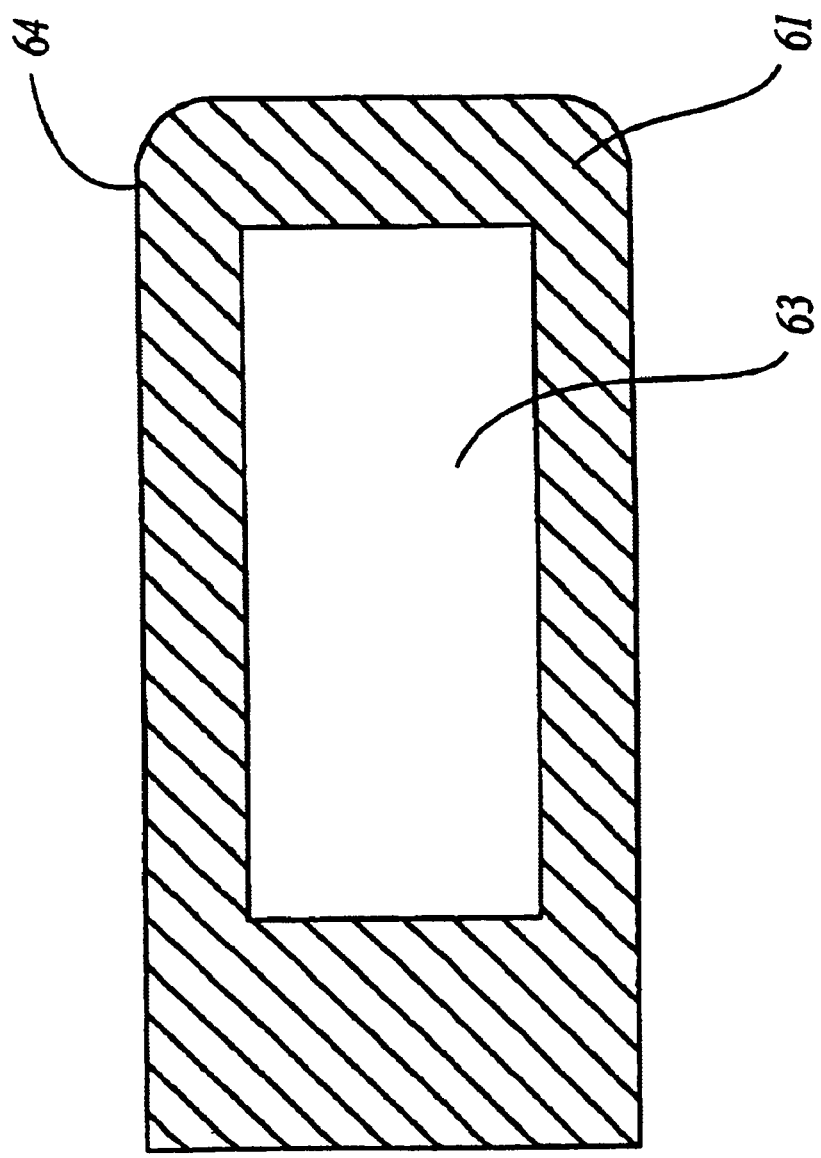
FIG. 12 is a top plan view of the heater.

In order to ensure uniform heating by thermal platform 60, the resistive heater 64 is bonded to the bottom side of plate 60. As stated, the brass plate has sufficient conductivity to smooth out any local non-uniformity caused by the fact that the heating traces are not continuous over the surface, but rather are adjacent lines separated by a space where no heat is generated. The separation is on the order of 0.015 inch, so this non-uniformity in the heat source is not seen at the other side of the brass plate. Uniformity of temperature of the slide may also be achieved by modifying the heating traces so that they produce heat in a non-uniform manner. Heat is lost to the surrounding air at all surfaces including the edges of the slide 37 and edges of brass plate 60. But heat is generated only in the heater 64 on the bottom surface of the brass plate. If the heat generation is uniform over the area of the heater so there is constant flux into the bottom of the brass plate, the center of the top of the glass slide will be significantly hotter than the edges where heat can dissipate faster. This phenomenon can be accommodated if the heater flux is less in the center so that the temperature uniformity on the top of the glass slide can be enhanced. A finite element heat transfer program, Mechanica by Parametric Technologies (Waltham, Mass.) may be employed to model the heat flow in the system. The heater flux is preferably set to be as shown in FIG. 12, where the central area 63 covers 40% of the total and generates 8.3% of the total energy while the outer zone area 61 generates the balance. Therefore, since the central area receives less heat, the temperature on the slide that is directly above the central area is slightly cooler than the temperature of the slide that is directly above the oblong ring. The variation in temperature over the useful area of the glass slide (the area upon which tissue is placed, which generally excludes the extreme edges of the slide) is about 0.2° C., when the heater is profiled as described. The temperature gradient from the center of the glass slide to an edge of the useful area of the glass slide is as follows: gradually rising 0.2° C. then gradually falling 0.2° C. The top surface of a wetted glass slide, which is one inch wide and three inches long, maintains a specified temperature uniformly over its useful area which is defined as the area centered on the width of the slide that is 0.75 inches wide, 1.6 inches long and starts 0.25 inches from the end opposite the label. The uniformity goal is to maintain a set temperature to within plus or minus two Celsius degrees over the useful area for any set temperature from 37° C. to 95° C.

In lieu of the aforementioned heating elements, a Peltier-type thermal transducer could be employed that is capable of both heating and cooling by reversing the polarity through the transducer. Such a cooling capability may have utility in connection with certain potential uses and applications of the present invention such as performing in-situ PCR (discussed hereinafter).

A temperature sensor 68 is also mounted within cavity 73 to the underside of heater 64. Several different types of sensors could be used such as thennistors, RTD's, or thermocouples. In a preferred embodiment of the present invention an integrated circuit sensor 68 providing direct temperature to digital conversion is used such as sensor model no.DS 1721 available from Dallas Semiconductor (Dallas, Tex.). This sensor uses the I'C. protocol to digitally report the sensed temperature. Similar sensors are available from National Semiconductor (Santa Clara, Calif.). The sensor selected must be accurate, repeatable, and have low thermal mass.

A housing 70, preferably constructed of an injection molded plastic, is provided for removably clamping heater/sensor unit 58 to carousel 34 and for supporting glass slides 37. As best viewed in FIG. 9, housing 70 defines a generally rectangular cavity 71 into which heater/sensor unit 58 may be inserted and held by a clamp. At bottom of housing 70 there is defined a recessed area 72 that receives a corresponding rim 74 defined along the terminal edge of skirt 62 to hold heater sensor unit 58 in place. To further seal cavity 71 from the various reagents used during operation of the apparatus, a downwardly extending lip 76 can be provided to more firmly engage rim 74. A bulge 78 may also be provided along the outer wall of skirt 62 for further sealing. The outside dimension of this bulge is slightly larger than the inside dimension of the housing, causing an interference that prevents liquids from entering cavity 71 below the bulge between the skirt and the housing.

The base of the housing defines a set of apertures 80 (FIG. 8) to receive machine screws that engage aligned bores defined in the carousel.

Figure 9:
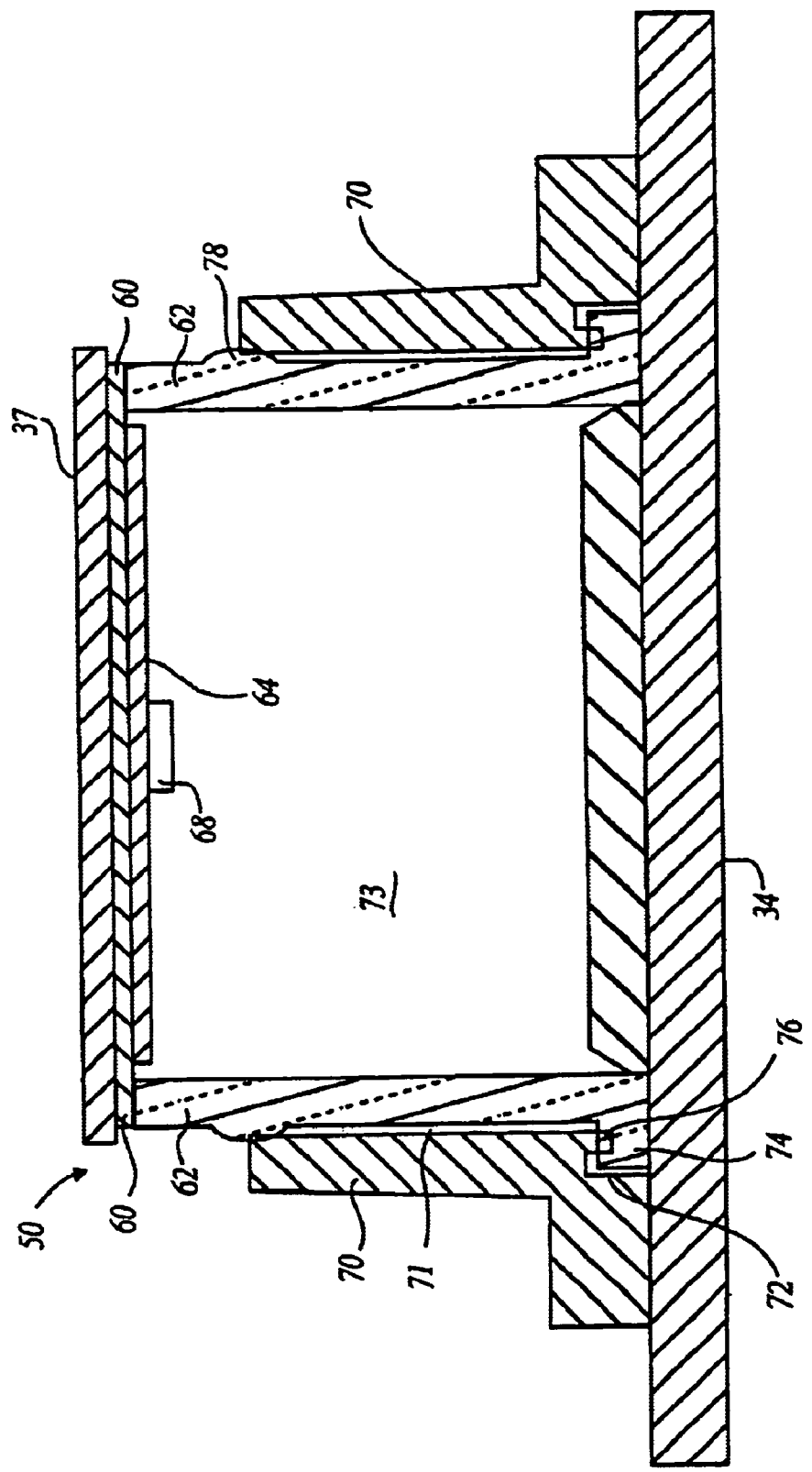
FIG. 9 is a cross section view of the thermal platform taken along line 9-9 of FIG. 8.
Figure 10:
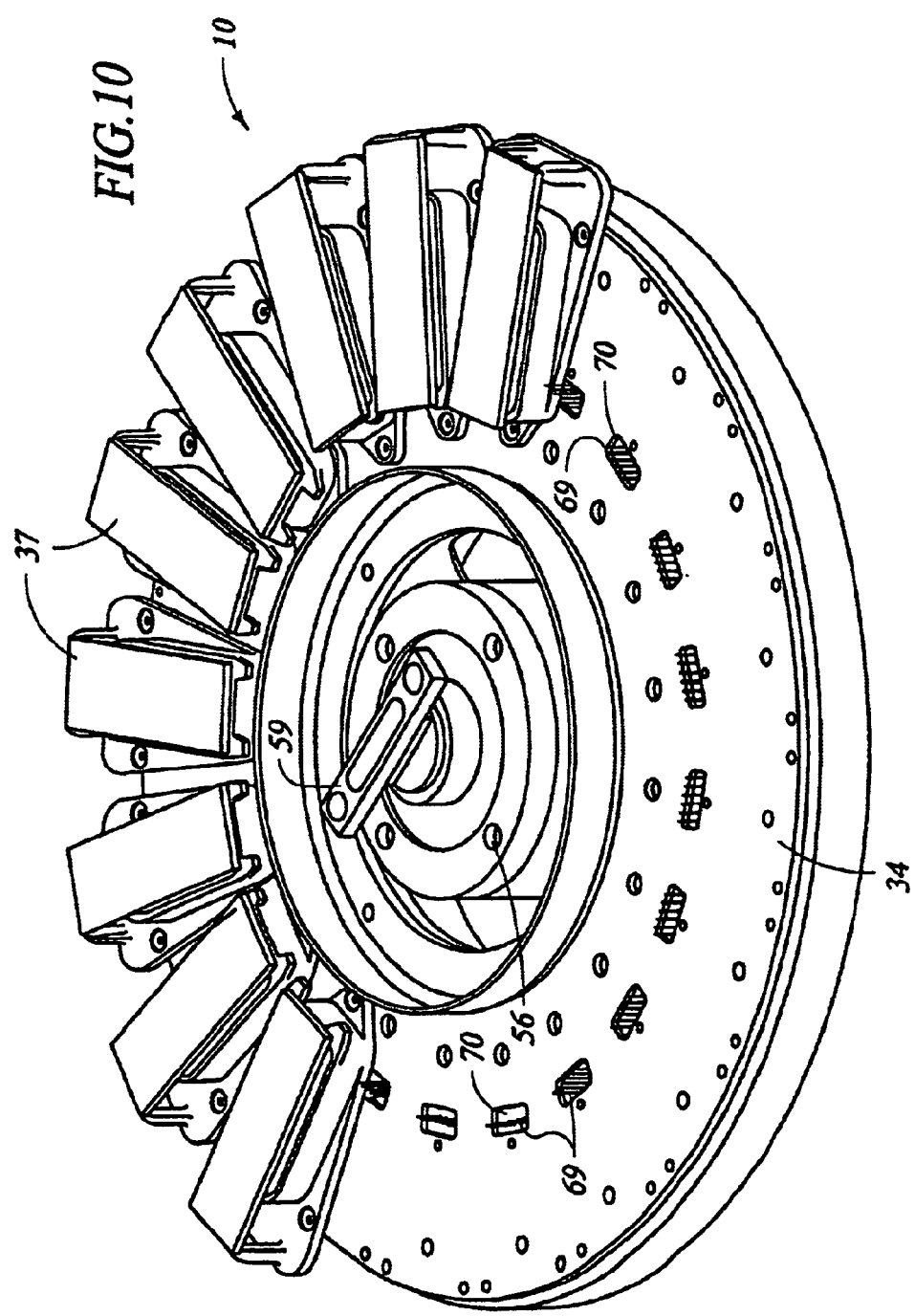
FIG. 10 is a perspective view of the slip ring assembly and slide carousel shown with a plurality of thermal platforms mounted thereto.

Glass slides 37 rest against plate 60 captured by four upwardly depending posts 82 which are integrally mounted to housing 70. The posts extend half way up the thickness of the glass slide 37 as can be seen in FIG. 9 since the glass slide is 0.04 inch thick, the posts are 0.02 inch below the top surface of the glass slide. It is important that the posts do project to the top surface of the slide in order to prevent surface tension of the aqueous solution from drawing the solution off. A problem with devices known in the art that vertically clamp against the top of the slide is that they have a tendency to wick fluid off of the slide by capillary action. It should be appreciated that other means for capturing or supporting the slides may be employed.

Control Electronics (Printed Circuit Board)

Figure 13:
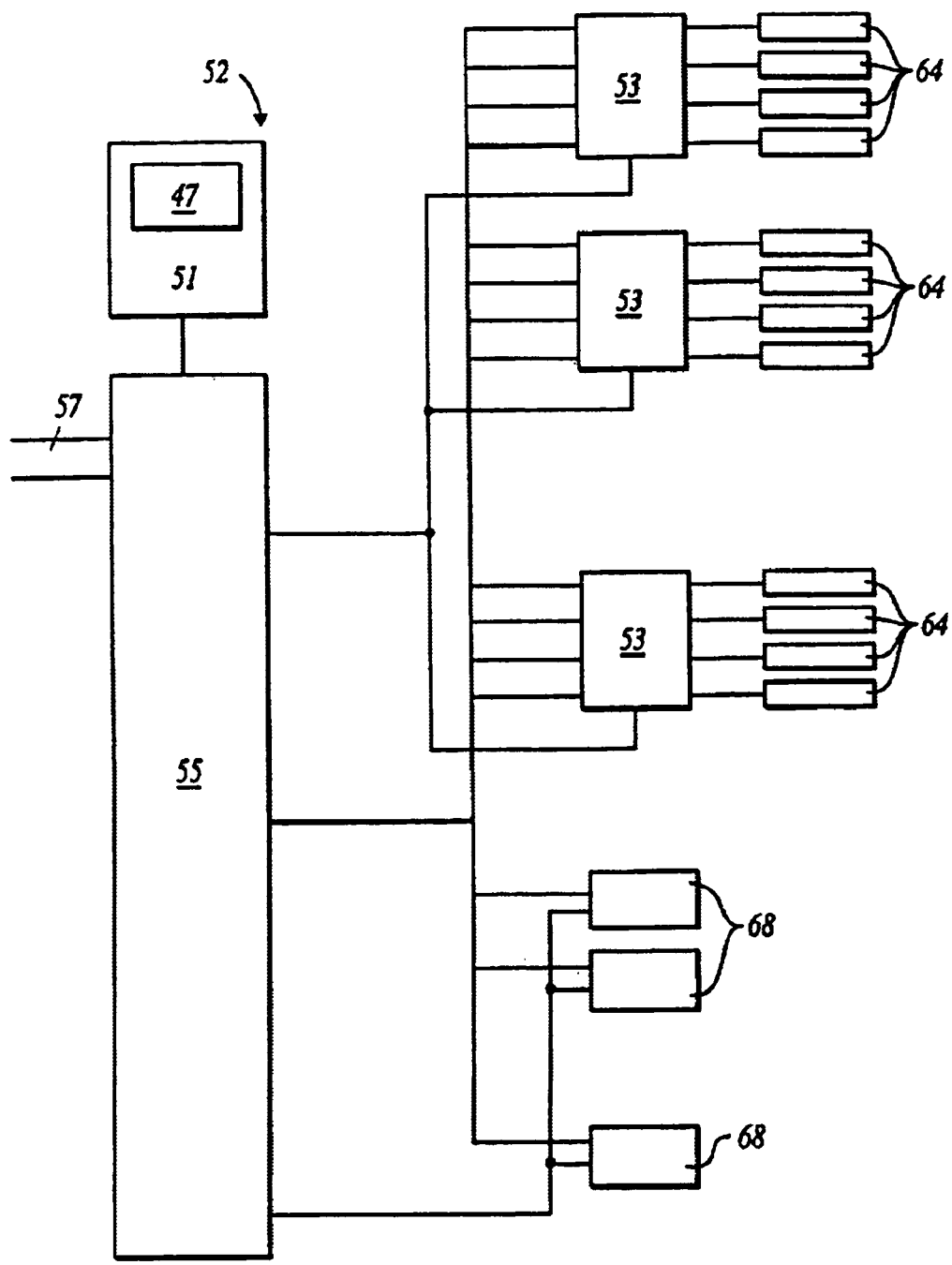
FIG. 13 is a block diagram of the control electronics, heaters and sensors as shown in FIG. 5.

With reference to the block diagram shown in FIG. 13, control electronics 52 consists of an annular printed circuit board with the components necessary to receive temperature setpoint information from staining apparatus microprocessor 44 via a serial digital protocol 57 and using this information to maintain each heater 64 at its setpoint. Not shown are those components (e.g. resistors, capacitors, etc,,) readily understood by one of skill in the art to be included The control of the heaters may be performed in a variety of methods. In a preferred embodiment, the heaters may be individually controlled by an integrated circuit driver or individual transistors 53 capable of switching the heater current on and off. Thus, the processor may control the duty cycle of the heaters, as described subsequently. In an alternate embodiment, the amount of power to the heaters may be regulated by processor 55 so that the heaters may be performed at a percentage of total capacity (e.g., 50% of maximum heating power). In a preferred embodiment, an integrated circuit (UDQ2559) available from Allegro Microsystems (Worcester, Mass.). Serial communication 57 with microprocessor 44 (via slip ring assembly 56) preferably uses the PC (Inter Integrated Circuit) serial bus protocol developed by Philips Labs, Eindhoven, The Netherlands. Alternative protocols could also be employed such as RS232D, RS422 or others. Control electronics 52 functions to both monitor the sensors 68 and control the heaters 64. Central to control electronics 52 is a microprocessor 55 (which is in communication with memory 51) or other digital circuitry of sufficient capability to communicate with staining apparatus microprocessor 44 via the $I^2C$ serial bus, monitor the heater temperature sensors 68 and power the heaters 64 when the slide temperature needs to be raised at a particular time. An example of such a microprocessor is PIC 16C64A available from Microchip Technology Inc., Chandler, Ariz. The program must control each heater in response to the heater temperature sensor when compared with the setpoint temperature (or target temperature) provided by the staining system microcontroller. (See FIG. 14). The microprocessor 55 determines, based on a look-tip table of the setpoint temperatures 47 in memory 51, how to control the heaters The setpoint temperatures in look-up table 47 are received from serial communication 57 with microprocessor 44. The microprocessor 55 obtains the actual temperatures from sensors 68, and thereafter modifies the control of the heaters 64 based on the difference in actual temperature and setpoint temperature. This control of the heaters may be strictly on-off (i.e., turn the heater on if its sensor temperature is below setpoint, and turn the heater off if its sensor temperature is above setpoint) or it may use proportional, integral, and/or derivative control system algorithms to provide a more controlled and accurate response.

The power distribution and controlling feedback system must be sufficient so that the thermal platform can be precisely regulated to mimic the features in thermocycling technology (e.g. in-situ PCR) and be capable of rapid temperature ramp-ups and cool-downs (e.g. from 37° C. to 95° C. in under 3 minutes and cool over the same range in under 5 min.). These features are particularly important for successful ISH staining.

Figure 14:
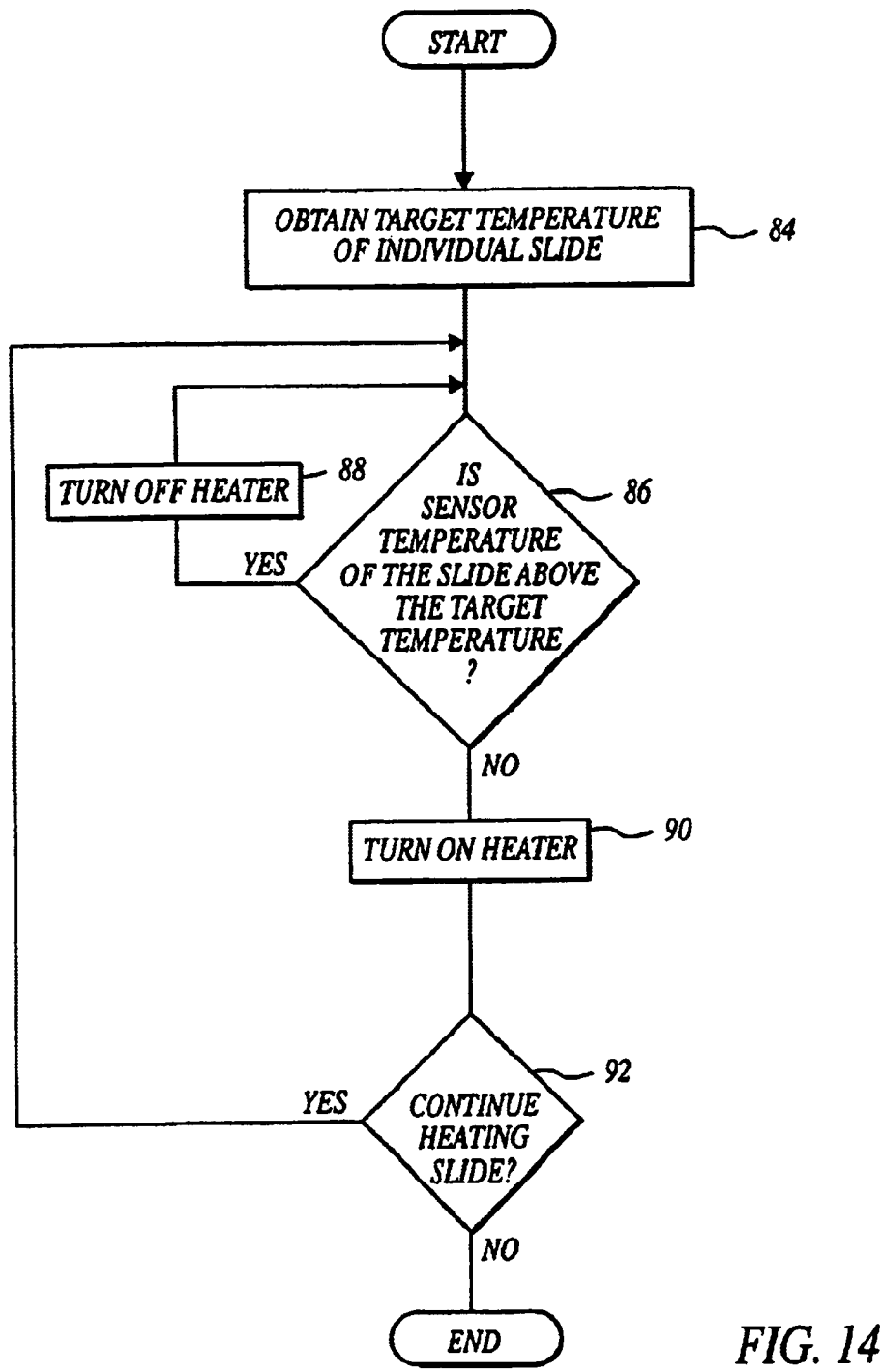
FIG. 14 is a flow chart of the controlling of the heating of an individual slide.

The processor controls the temperature of the slides by modifying the heat to the slides in order for the slides' temperature to be at the target temperature. In a preferred embodiment, modifying the heat to the slides is accomplished by modifying the output of the heaters. Referring to FIG. 14, there is shown a flow chart of the control of the heating of the individual slides. As shown at block 84, the target heating temperature (or setpoint temperature) for the individual slide is obtained. In the preferred embodiment, the target temperature is sent from microprocessor 42 to the control electronics 52. The target temperature may alternatively be input from the operator or be read through the barcode on the slide. As shown at block 86, it is determined whether the temperature of the slide, as indicated by temperature sensor 68, is above the target temperature. If yes, the heater is turned off, as shown at block 88. Alternatively, depending on the disparity between the actual temperature and the target temperature, the amount of heat generated by the heater may be modified. For example, the duty cycle for the heater may be reduced. Through pulse width modulation, the duty cycle for the heater may be modified (e.g., the duty cycle for the heater may be reduced from 50% (where the heater is on 50% of the time) to 25% duty cycle (where the heater is on 25% of the time)). In another alternative embodiment, the cooler can be turned on after the heater is turned off, if the actual temperature is significantly greater than the target temperature or if finer temperature control is sought.

In still another alternative embodiment, the processor may control the amount of heat transferred to the slide by modifying the amount of heat transferred between the heater and the slide. As one example, the microprocessor may change the heat transmission characteristics of a buffer between the heater and the slide, thereby modifying the amount of heat transferred to the slide, and thereby modifying the temperature of the slide.

If the temperature of the slide is less than the target temperature, the heater is turned on, as shown at block 90. The control of the heater may use proportional, integral, and/or derivative control system algorithms to provide a more controlled and accurate response. In a preferred embodiment, the amount of heat generated by the heater is based on the disparity between the actual temperature and the target temperature. For example, depending on the disparity in the temperature between the current temperature and the target temperature, the heater may be turned on for a 100%, 50%, etc. duty cycle. Thus, if the actual temperature is greater than 2° C. away from the target temperature, the heater is turned on with a full duty cycle. As the actual temperature approaches the target temperature, the duty cycle of the heater is reduced, thereby generating less total heat for the slide. In addition, once the heater achieves the target temperature, the processor 55 maintains control by determining the difference between the actual temperature and the target temperature, as shown at block 86. This loop is continued until the time for heating of the slide is over, as shown at block 92. Thus, if the slide is scheduled to be heated for a predetermined amount of time, the control of the temperature of the slide is performed until the predetermined amount of time has elapsed.

Moreover, based on the particular target temperature of a slide, it has been determined empirically the amount of heat necessary to maintain the slide at the target temperature. For example, when the amount of heat is modified based on modifying the duty cycle of the heaters, the particular duty cycle for the heater has been determined based on the target temperature. These values are stored in look-up table 47. Thus, as the actual temperature of the slide approaches the target temperature, the duty cycle is reduced to the empirical value in look-up table 47. In this manner, the temperature of the slide may be transitioned from the current temperature to the target temperature.

Alternatively, the control of the temperature may be strictly on-off (i.e., turn the heater on if its sensor temperature is below target temperature, and turn the heater off if its sensor temperature is at or above the target temperature) or the control of the temperature may be proportional (i.e., modifying the amount of heat generated by the heater instead of the duty cycle so that the heater outputs a portion of its total heating power, e.g., 50% of its total heater output).

Figure 15:
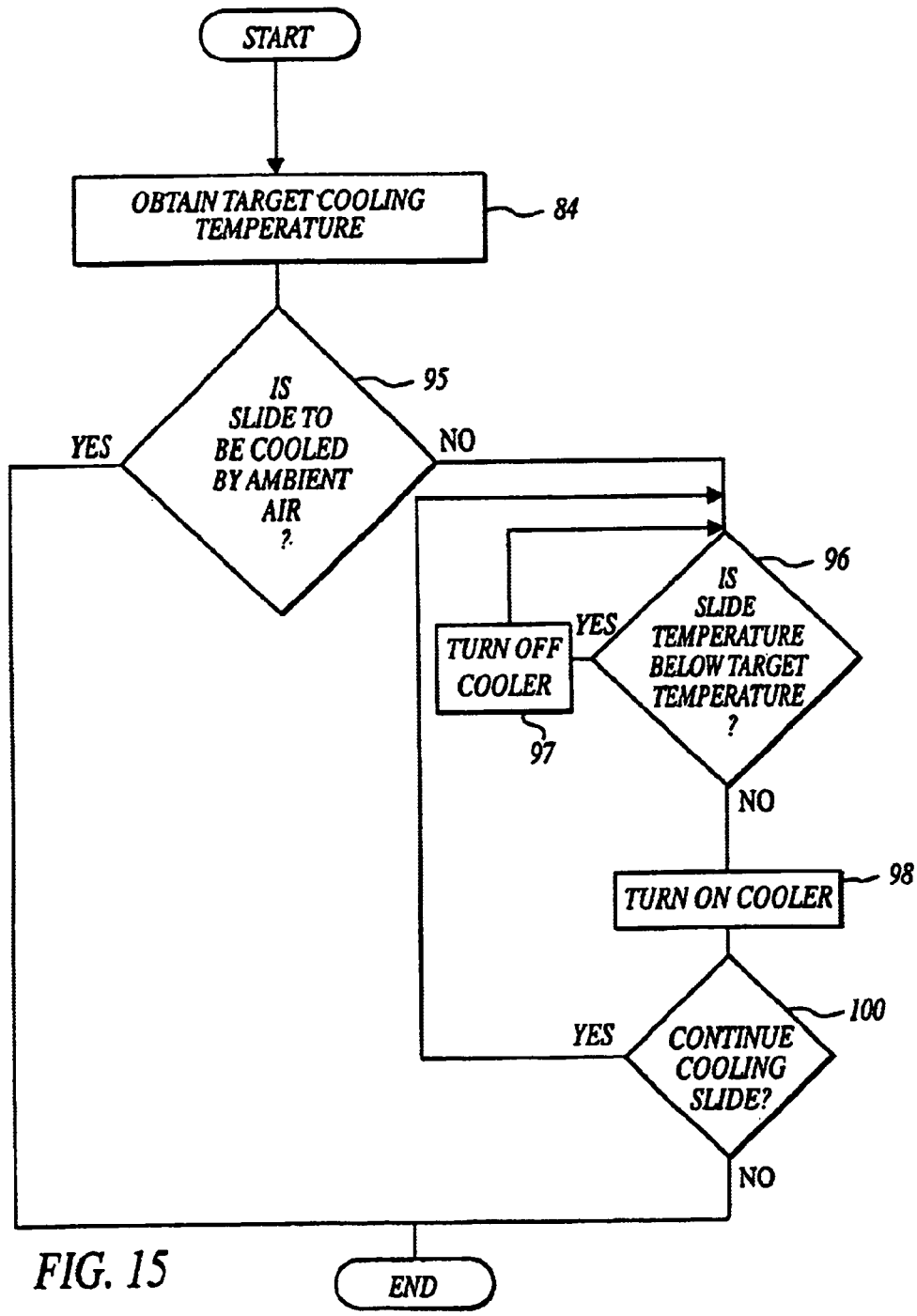
FIG. 15 is a flow chart of the controlling of the cooling of an individual slide.

Referring to FIG. 15, there is shown a flow chart of the control of the cooling of the individual slides as an alternate embodiment of the invention. As shown at block 94, the target cooling temperature for the individual slide is obtained. The target temperature is sent from microprocessor 42 to the control electronics 52. The target temperature may alternatively be input from the operator or be read through the barcode on the slide. As shown at block 95, depending on the operation of the system, the slide may be cooled by the ambient air, or alternatively be cooled by cooling platforms or the like.

As shown at block 96, similar to FIG. 14, it is determined whether the temperature of the slide, as indicated by temperature sensor 68, is below the target temperature. If yes, the cooler is turned off, as shown at block 97. Alternatively, depending on the disparity between the actual temperature and the target temperature, the cooling amount generated by the cooler may be modified. For example, the duty cycle for the cooler may be reduced. Through pulse width modulation, the duty cycle for the cooler may be modified.

If the temperature of the slide is greater than the target temperature, the cooler is turned on, as shown at block 98. The control of the cooler, similar to control of the heater, may use proportional, integral, and/or derivative control system algorithms to provide a more controlled and accurate response. In one embodiment, the cooling force generated is based on the disparity between the actual temperature and the target temperature. For example, depending on the disparity in the temperature between the current temperature and the target temperature, the cooler may be turned on for a 100%, 50%, etc. duty cycle. Thus, if the actual temperature is greater than 2° C. away from the target temperature, the cooler is turned on with a full duty cycle. As the actual temperature approaches the target temperature, the duty cycle of the cooler is reduced, thereby generating less total cooling energy for the slide. In addition, once the cooler achieves the target temperature, the processor 55 maintains control by determining the difference between the actual temperature and the target temperature, as shown at block 96. This loop is continued until the time for cooling of the slide is over, as shown at block 100.

Slip ring Assembly

Figure 11:
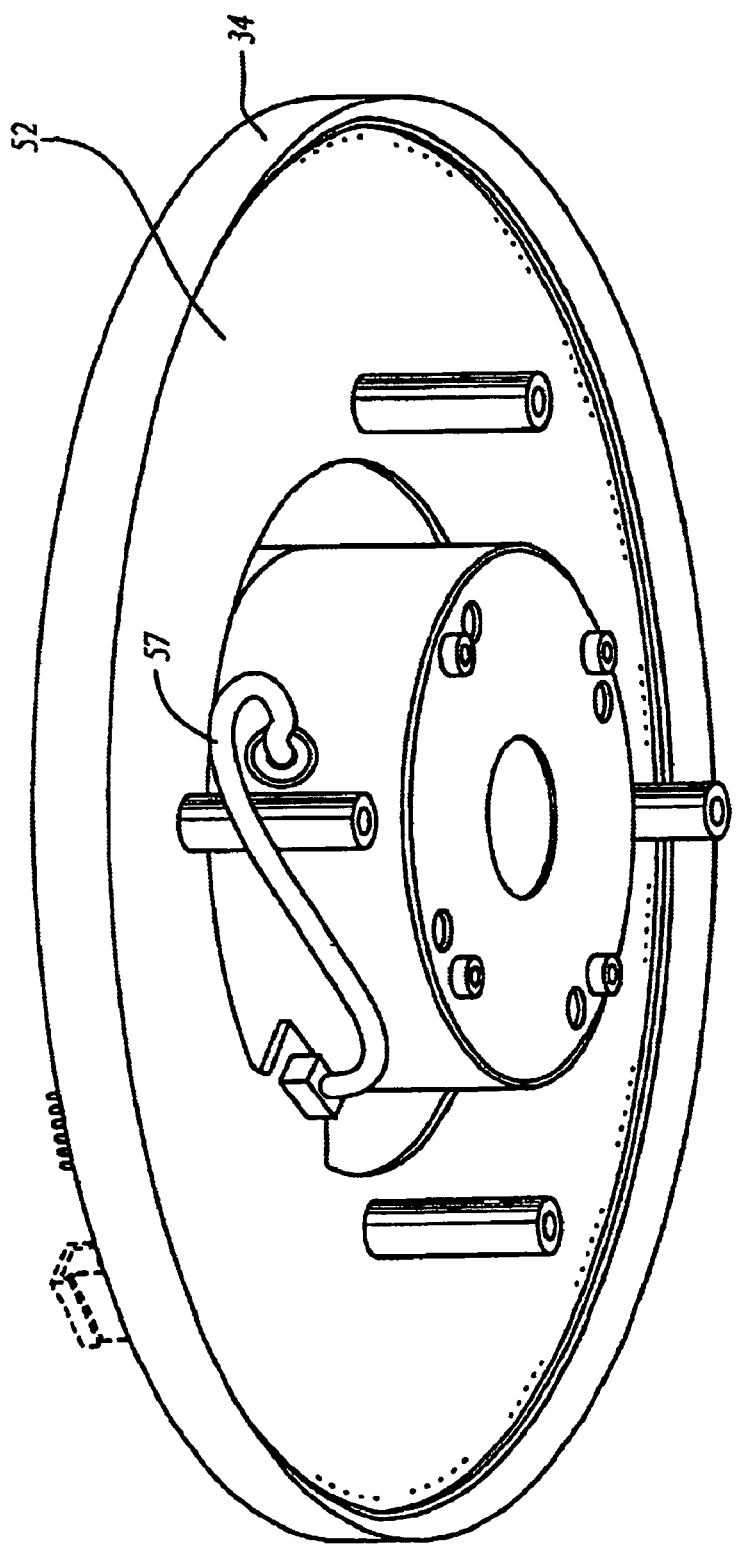
FIG. 11 is a perspective view of the underside of the carousel shown in FIG. 10 shown with the control electronics printed circuit board mounted thereto.
Figure 16:
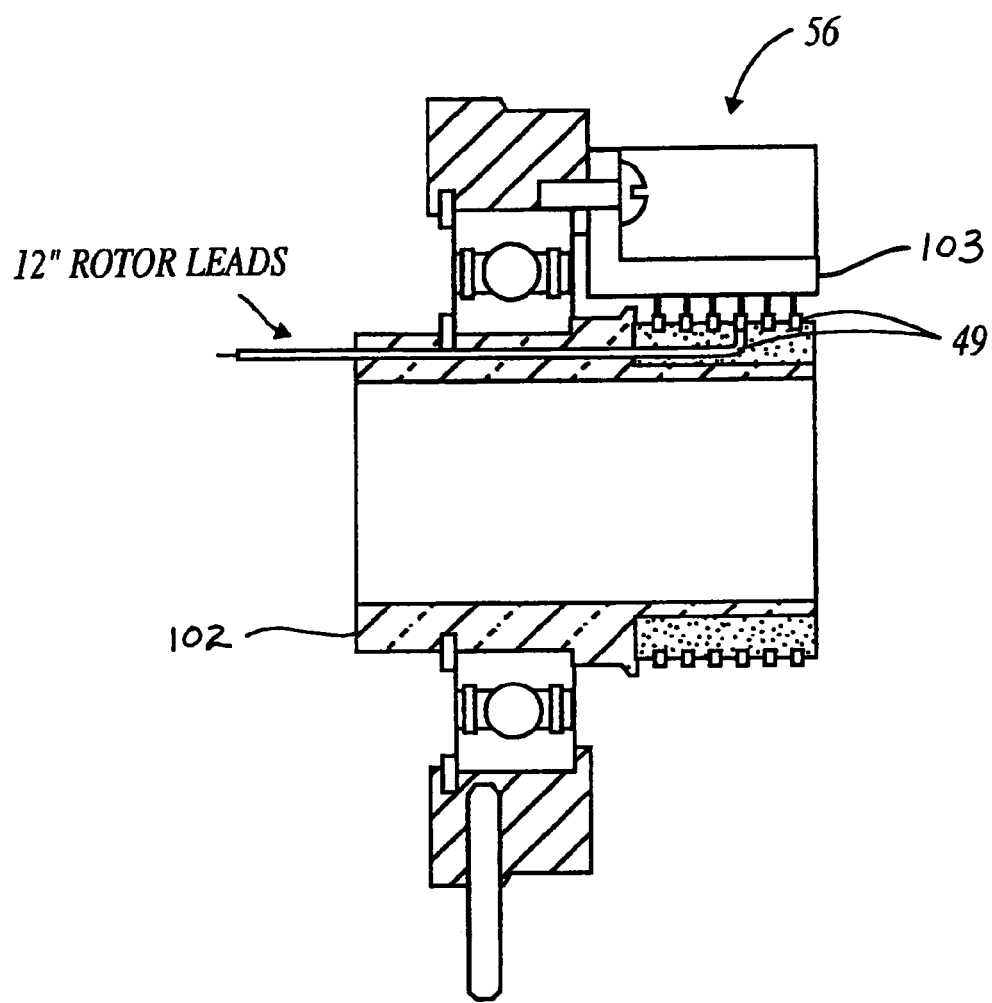
FIG. 16 is a cross section view of the a slip ring assembly.

Slip ring assembly 56 uses technology employing rotating silver slip rings 100 and silver graphite brushes 101. Rings 100 and graphite brushes 101 allow rotor 102 and stator 103 to remain in physical contact with one another even while rotor 102 moves relative to stator 103. The slip ring must be of sufficient size (about 3" diameter) and capacity (about 10 amps per circuit) to carry the $I^2C$ digital control signals (two circuits), power to the logic (two circuits), and power to the heaters (two circuits). Slip ring assemblies suitable for this application are available from Fabricast, Inc, South El Monte Calif., Airflyte Electronics, Bayonne, New Jersey, Litton Poly-Scientific, Blacksburg, Va. and others. A cable 57 operably connects slip ring rotor 102 to the control electronics 52 (FIG. 11). A stator bracket 59 is provided to mount stator 103 to apparatus 10 using machine screws or the like (mounting not shown). Referring to FIG. 16, there is shown a longitudinal section view of the slip ring assembly 56, with leads 49 which transmit data, logic power and heater power, as shown in FIGS. 5 and 16. Moreover, a roller bearing 104 is located between the slip ring 102 and stator 103 to provide for the relative movement of rotor 102 with respect to stator 103.

In general, the slip ring assembly includes a first portion and a second portion wherein the first portion is movable while the second portion remains stationary with respect to apparatus 10. For purposes of this invention, the first portion may be either rotor 102 or stator 103. Thus, depending upon the apparatus configuration, rotor 102 may move while stator 103 remains stationary or, alternatively, rotor 102 may remain stationary while stator 103 moves.

Figure 3:
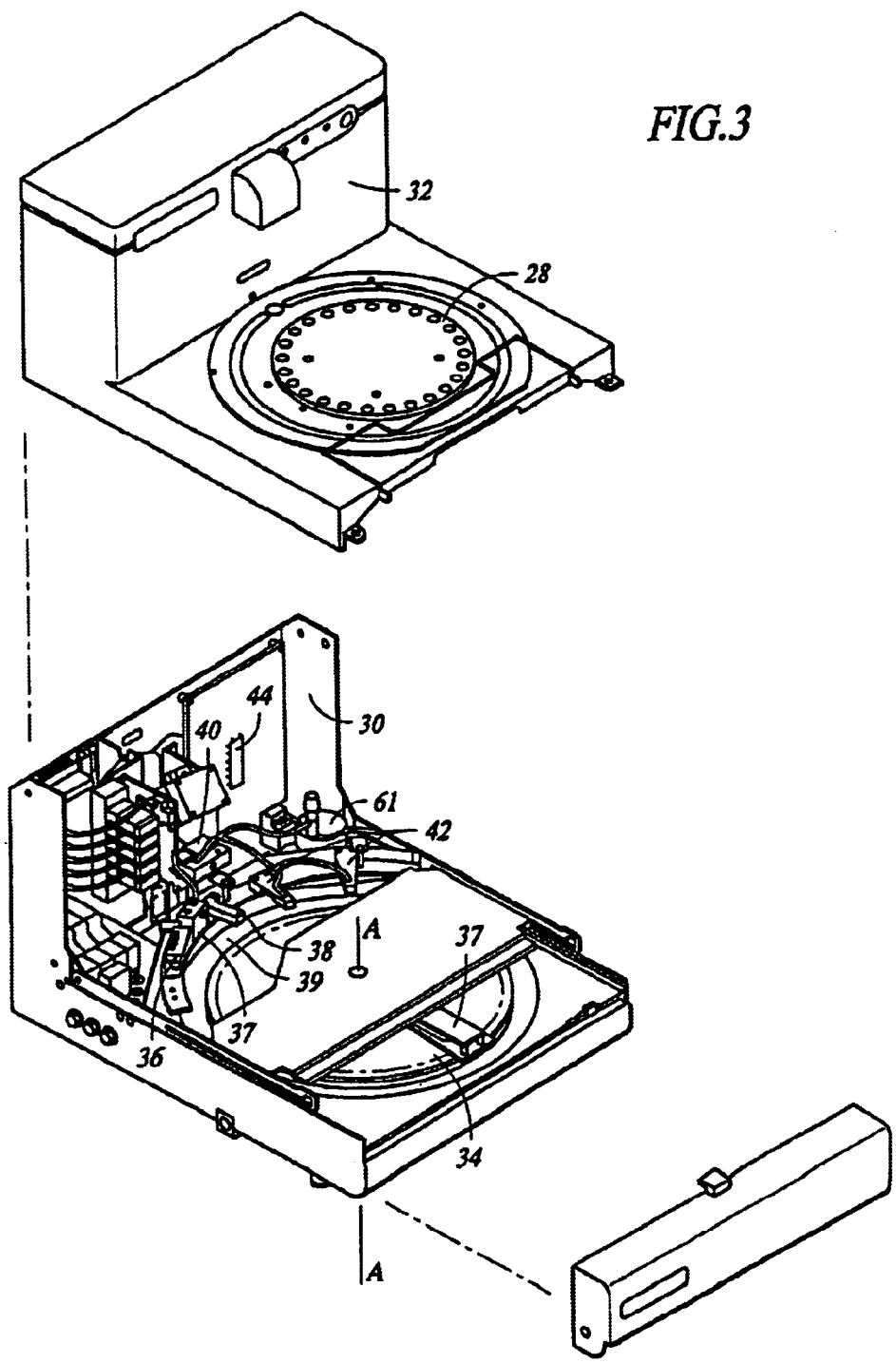
FIG. 3 is an exploded view of the present invention.

With reference to FIG. 3 the following components are mounted within apparatus 10 generally as described in U.S. patent application Ser. No. 08/995,052: Liquid Coverslip™ dispense nozzle 37, stepper motor 61, rinse dispense nozzles 36, fluid knife 38, bar-code reader 40, air vortex mixers 42, and wash volume adjust 39. The buffer heater as disclosed in the above-referenced application has been removed. Bulk fluid module 22 (FIG. 2) is preferably constructed to accommodate a plurality of fluid receptacles as needed for ISH including SSC, DI water, and cell conditioning buffers. The volume adjust nozzle 39 is constructed to permit application of the plurality of fluids.

The invention herein also departs from the one disclosed in U.S. patent application Ser. No. 08/995,052 in the manner in which the wash buffer is wiped off the slide after being applied so as not to dilute the next reagent applied. With the present invention nozzle 36 is aimed to spray fluid at the end of the slide from which the fluid is to be evacuated thereby causing evacuation of the fluid through capillary action.

Figure 17:
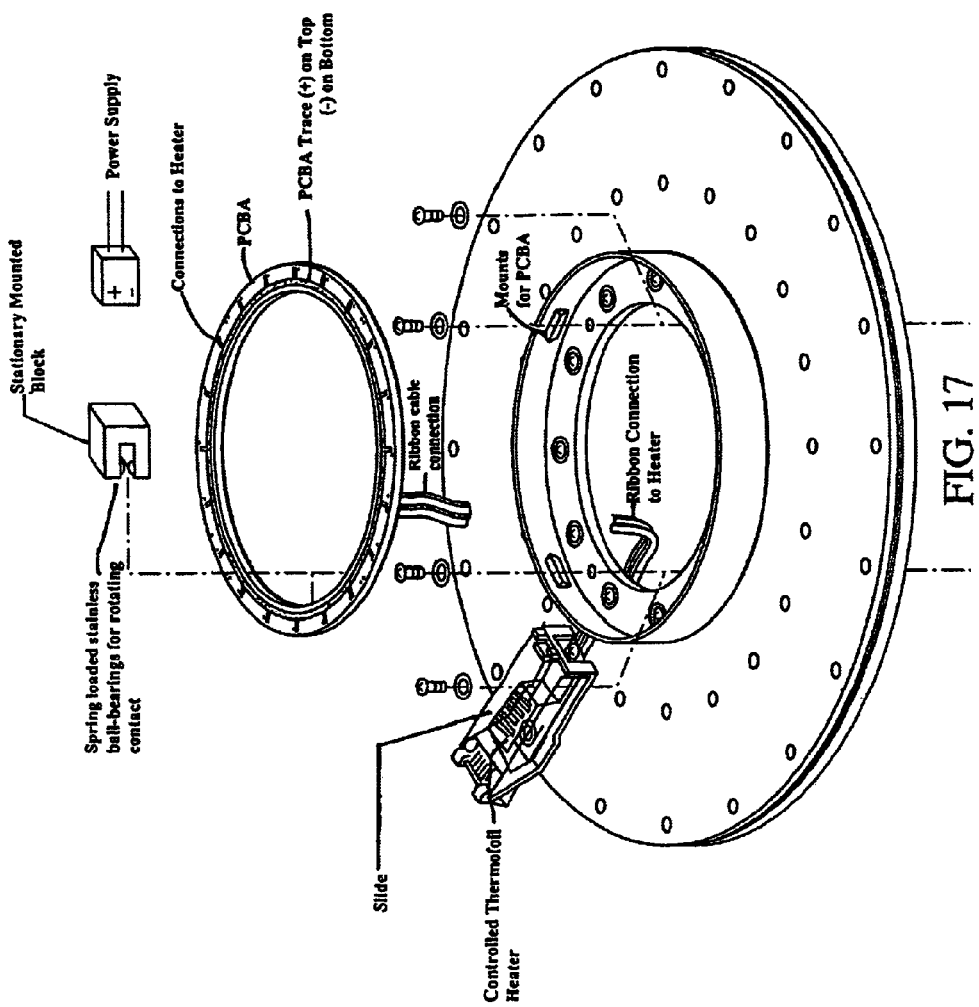
FIG. 17 is an exploded view of the assembly including the slip ring, printed circuit board assembly (PCBA), the carousel, and the thermofoil heater.
Figure 18:
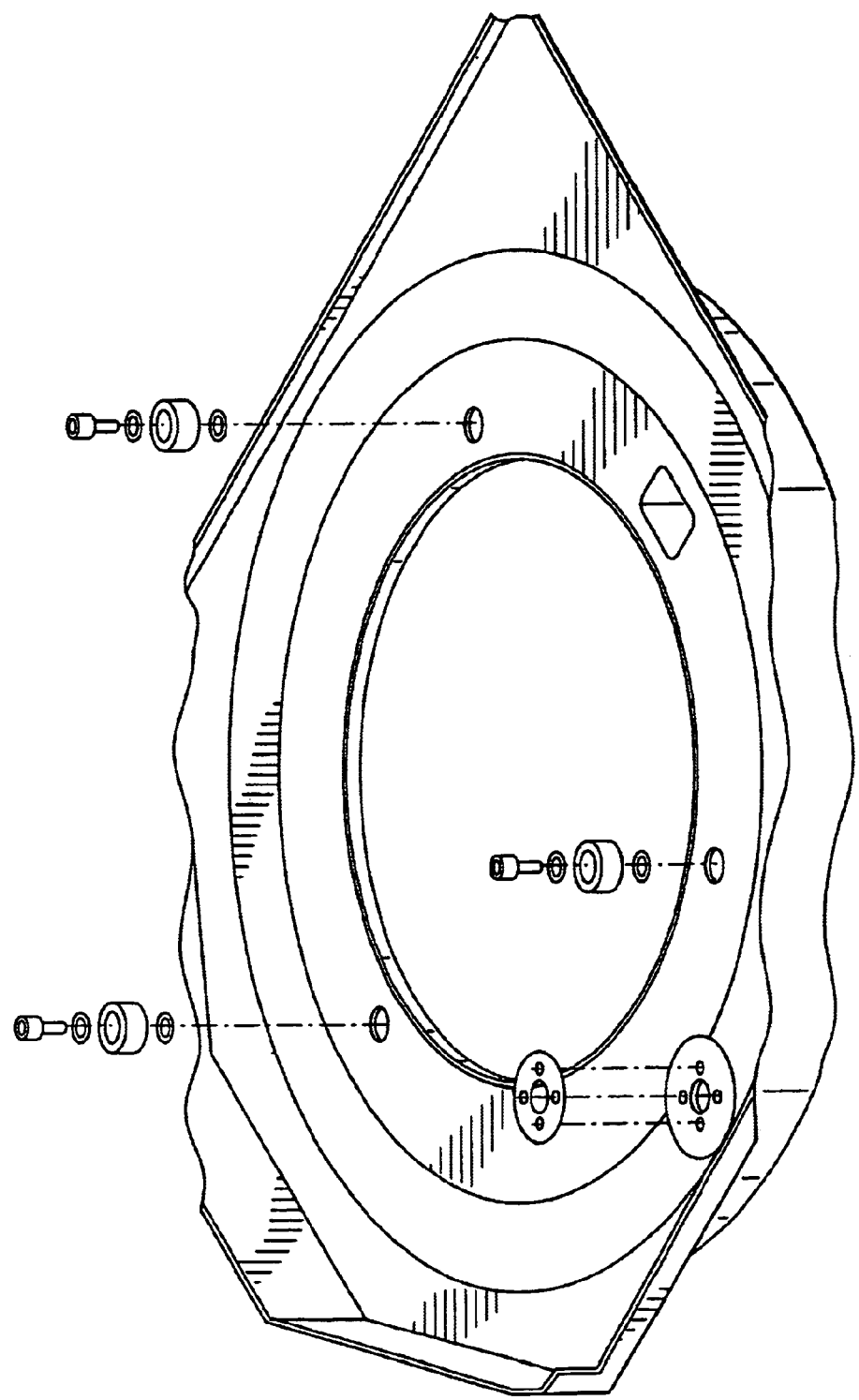
FIG. 18 is a top perspective view of a tub where any of the overflow or reagents goes into.

An alternative embodiment of the slip ring assembly is shown in FIGS. 17-23. Referring to FIG. 17, there is shown an exploded view of the assembly including the slip ring, printed circuit board assembly (PCBA), the carousel, and the thermofoil heater. In order to maintain constant power to the thermofoil assembly, the stationary block is mounted to contact the PCBA. The PCBA rotates as the carousel rotates, so that there is constant power to the ring (due to contact with the stationary block). This, in turn, gives constant power to the thermofoil heater since there are wires go from the thermofoil heater to the printed circuit board assembly (PCBA). Referring to FIG. 18, there is shown a tub where any of the overflow of reagents goes into. The tub further includes a drain.

Figure 23:
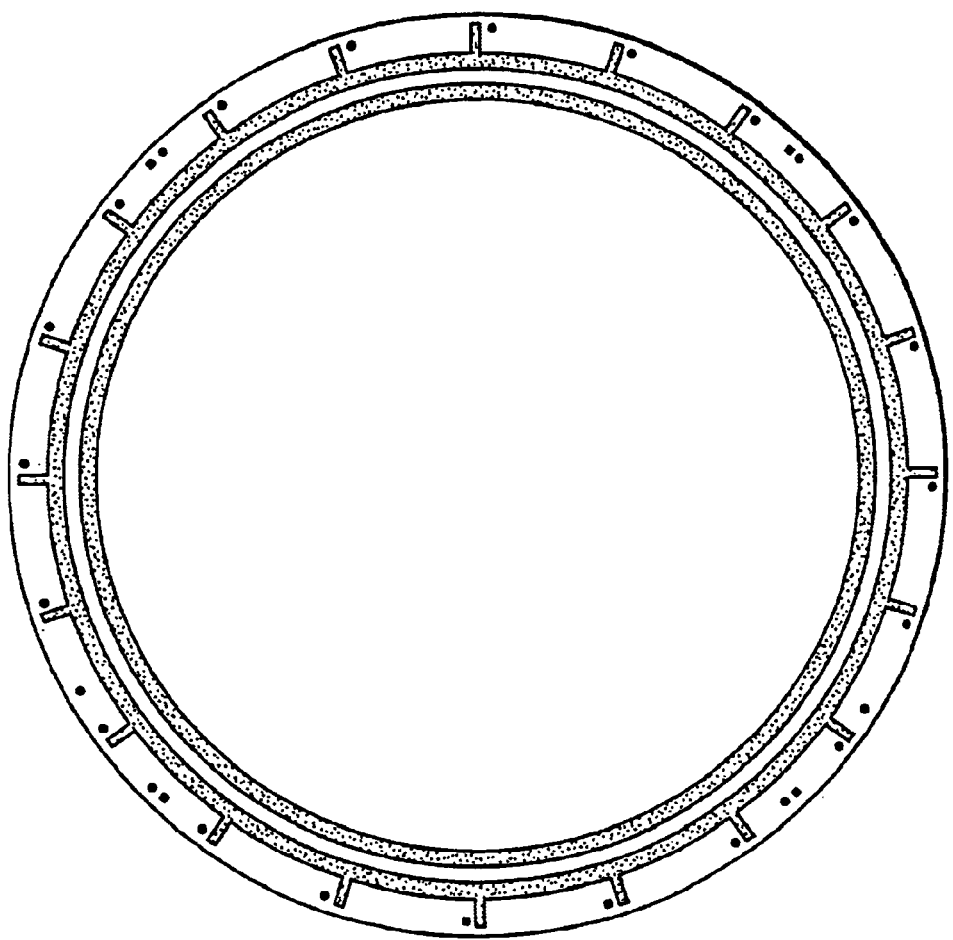
FIG. 23 is a Power Ring PCBA.

The purpose of the Power Ring PCBA, as shown in FIG. 23, is to provide a means for maintaining electrical contact with the slide turntable as it rotates within the unit. The ring has two pairs of conductors, one high current pair for the heaters and another low current pair for monitoring signals. The power traces are 0.125" wide and are on the top layer and the other on the bottom. The signal traces are 0.100" wide and are separated from the power traces by 0.075". Both the top and bottom layers are 2 ounces copper. To connect to the side heaters, 0.5" wide traces run approximately 0.15" from the power traces to pairs of pads at each of the 20 heater positions. A heater connects to the pads via several inches of 30 gauge wire, as supplied with the heater. When the circuit is energized, 24 VDC is applied to the power traces through top and bottom board contacts. Current flows through the power traces to the 78.4 ohm heaters distributed around the board.

The limiting factor is current carrying capacity of a PCB trace is the allowable temperature rise. This is calculated by defining the worst case ambient temperature the board will be operating in and the subtracting that value from the maximum allowable temperature of the PCT. (Worst case computing environment: 60 deg C.; FR4 maximum operating temperature: 120 deg C.; Maximum temperature rise of trace: 120 deg C.-60 deg C.=60 deg C.).

The current for the heaters flows through pairs of traces dedicated to each heater. Heater impedance: 78.4 ohms–10%=70.6 ohms; Heater trace current: 24 V/70.6 ohms–340 mA; Heater trace temperature rise from table: <1 deg C. Power trace width: 0.125"; Power trace cross section from table: 320 sq mils; Power trace current: 340 mA*20=6.8A; Power trace temperature rise from table: <10 deg C.; Power trace current margin: 21 A–6.8=14.2 A; Power trace temperature margin: 60–10=50 deg C.°.

Separation of the power traces and signal traces is 0.07". However, vias are necessary to route the signal traces to inner layers so they can reach the outer edge of the board. This vias are located within the 0.075" separation area, thus reducing the electrical separation to 0.040". The minimum allowable conductor spacing can be found from Table 3-1 in IPC-D-275. For this analysis, the vias are assumed to be bare although solder mask coating allows a closer minimum spacing. Maximum power trace to signal via voltage differential: 24 V–0 24 V; Minimum spacing for conductors from table: 0.025"; Actual power trace to signal via spacing: 0:40"; Conductor spacing margin; 0.040"–0.25"=0.015".

Figure 19:
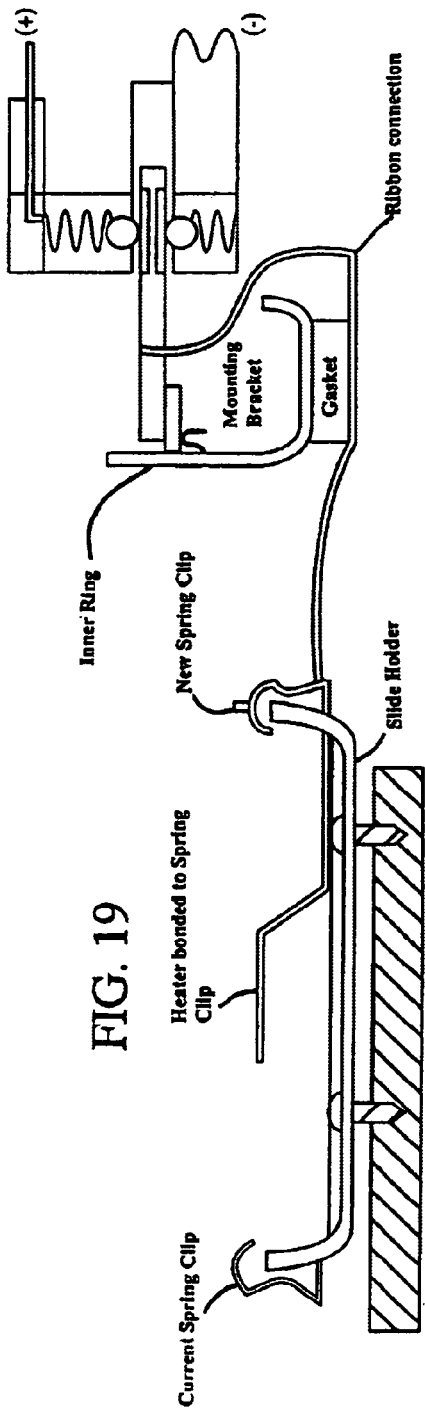
FIG. 19 is a cross sectional view of FIG. 17.

Referring to FIG. 19, there is shown a cross sectional side view of FIG. 17. As shown in FIG. 19, there are ball bearings 201, which are part of the stationary mounted block 202, that physically contact that PCBA. The ribbon connection 203 is a wire which is attached to the carousel which is attached to the heater. In practice, everything to the left of the ball bearings moves will roll as the carousel rolls so that continuous physical contact, and thereby continuous power is provided. The heater is bonded to the spring clip using glue or some other form of adhesive. To adjust the angle of the slide, a new spring clip, as shown in FIG. 19, may be included. The new spring clip may thereby place the slide at a slight declination, if necessary.

Figure 20B:
FIG. 20B is a side view of the PCBA along line A-A as shown in FIG. 20A.
Figure 20A:
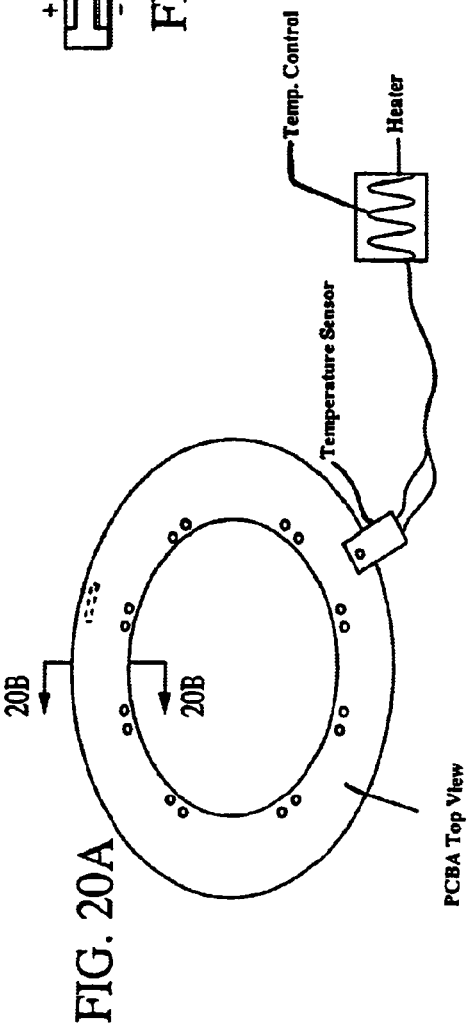
FIG. 20A is shown a top view of the PCBA.
Figure 21:
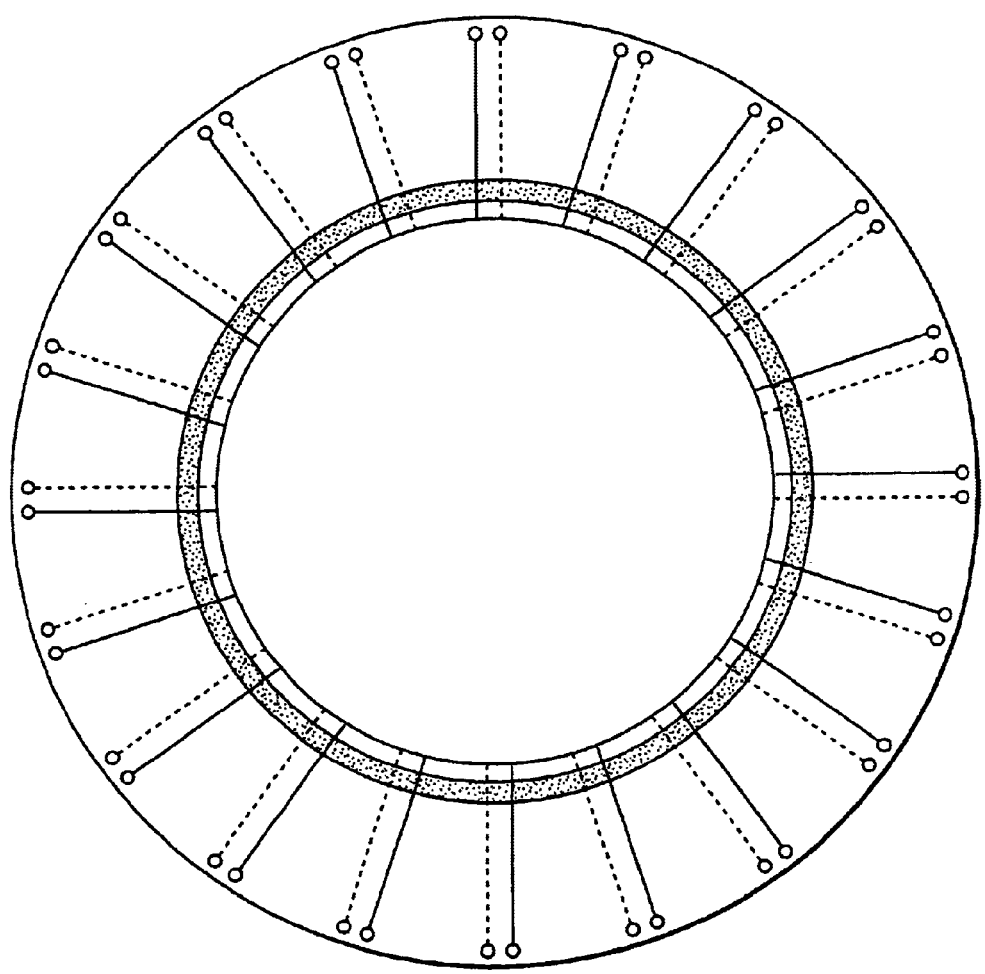
FIG. 21 is a top view of the PCBA.
Figure 22A:
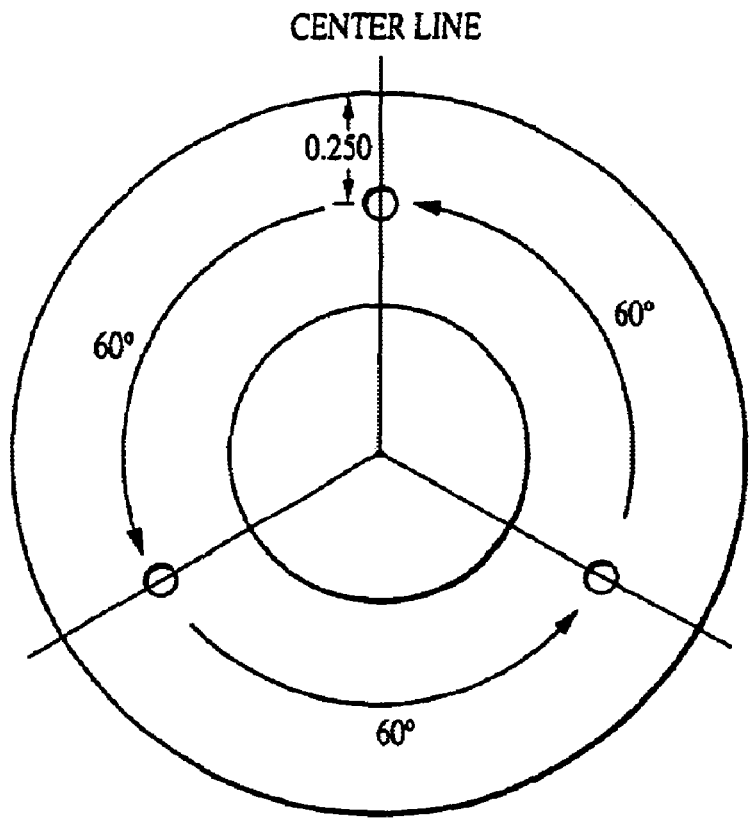
FIG. 22A is a top view of the PCBA with mounting holes.
Figure 22B:
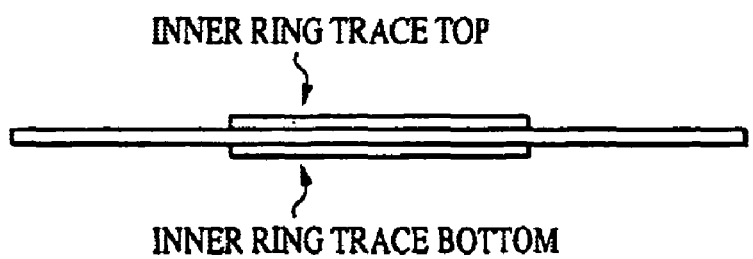
FIG. 22B is a side view of the PCBA with the positive (top) and negative (bottom) contacts for the inner ring trace.

Referring to FIG. 20A, there is shown a top view of the PCBA. FIG. 20B shows a side view of the PCBA along line A-A. There is a heater which is connected to the PCBA. The heater includes a sensor which is mounted on the PCBA in order to provide feedback to the heater. In this manner, the heater may provide closed loop control of the heating of the system. Referring to FIG. 21, there is shown a top view of the PCBA. Referring to FIG. 22A, there is shown another top view of the PCBA with mounting holes. Referring to FIG. 22B, there is shown a side view of the PCBA with the positive (top) and negative (bottom) contacts for the inner ring trace.

Definitions

The following terns shall have the following meanings as used herein:

"Tissue" means any collection of cells that can be mounted on a standard glass microscope slide including, without limitation, sections of organs, tumors sections, bodily fluids, smears, frozen sections, cytology preps, and cell lines.

"Targeted molecules" means detectable molecules found in cells including without limitation nucleic acids, proteins, carbohydrates, lipids, and small molecules.

"Stain" means any biological or chemical entity which, when applied to targeted molecules in tissue, renders the molecules detectable under a microscope. Stains include without limitation detectable nucleic acid probes, antibodies, and dyes.

"Treating" or "Treatment" shall mean application of a stain to a tissue as well as other processes associated with such application including, without limitation, heating, cooling, washing, rinsing, drying, evaporation inhibition, deparaffinization, cell conditioning, mixing, incubating, and evaporation.

"Automated" or "Automatic" means activity substantially computer or machine driven and substantially free of human intervention.

Use and Operation

In operation, apparatus 10 may be used to perform in-situ hybridization (ISH), in-situ PCR, immunohistochemistry (IHC), as well as a variety of chemical (non-biological) tissue staining techniques. Moreover, two or more of the above techniques may be employed during a single run despite their differing temperature requirements due to the inventive heating system herein.

In-situ hybridization is clearly a technique that may be advantageously employed with the present invention, either alone or in combination with other techniques, since many of the steps in ISH must be carefully temperature controlled for a precise period of time. The precise amount of heat for a specific period of time is necessary to sufficiently denature the DNA so that subsequent hybridization may occur without over-heating to the point where cell morphology is degraded. Different specimens may require different temperatures for denaturation depending on how the tissue was prepared and fixed. The steps of denaturation, hybridization, and posthybridization washes each have unique temperature requirements that depend on the particulars of the probe and tissue being tested. These temperature requirements can be controlled through the individualized control of the heaters, as discussed previously DNA probes require and are typically hybridized at between 30°-55° C. while RNA probes are typically hybridized at higher temperatures with the time for hybridization varying from 30 min. to 24 hours depending on target copy number, probe size and specimen type. Standard denaturation for cytogenetic preparations is performed at about 72° C. for 2 min. while for tissue sections the conditions may vary from 55° C. to 95° C. from 2 to 30 min. Post hybridization wash temperatures may vary from about 37° C. to 72° C. for 2 min. to 15 min. Salt concentration may vary from 0.1× to 2× SSC. Probe detection temperatures may vary from ambient to 42° C. for 2 min. to 30 min.

The low mass of the plate 60 and heater 64 enables the rapid heating and cooling of the slide and consequently the tissue on the slide (i.e. from 37° C. to 95° C. in 180 seconds). The increased rapidity of heating and cooling increases the efficiency of in situ hybridization. The rapid annealing of the probe to the target facilitated by rapid temperature ramping increases the specificity of the probe. Concomitantly, the background is decreased and the quality of the resulting test is vastly improved. ISH may be employed to detect DNA, cDNA, and high copy MRNA. It can be applied to smears, tissue, cell lines, and frozen sections. Typically, the specimen is mounted on a 1"×3" glass slide.

Hybridization or denaturation of DNA is absolutely essential to the tissue staining process and requires that temperatures in the range of 92-100 degrees C. be quickly reached, precisely controlled and maintained. The thermal platform brings treated tissue on microscope slides to the required temperature range in less than 180 seconds with an accuracy of plus or minus 2 degrees C. Rapid loss of temperature in hybridized tissue is essential to successful staining and diagnosis. A fan or other rapid cooling feature may be added to bring the required temperature to 37 degrees C. in less than 420 seconds.

The inventive apparatus permits the placement of multiple types of specimens and ISH tests in the same run without compromising the unique requirements of each ISH test requirement (i.e., hybridization temperature 37-45° C. stringency, and wash concentrations). The system may run more than one detection chemistry in the same run on different slides. As used herein "ISH" includes both fluorescent detection (FISH) and non-fluorescent detection (e.g. brightfield detection).

Apparatus 10 may also be employed for the simultaneous application of ISH and IHC staining to certain tissue sections to allow both genetic and protein abnormalities to be viewed at the same time. This may be advantageous, for example, in assaying breast tumor sections for both gene amplification and protein expression of HER-2/neu as both have been deemed to have clinical significance. See Ross et al. "The Her-2/neu Oncogene in Breast Cancer," *The Oncologist* 1998; 3:237-253.

The rapid heating and cooling by the thermal platform make the present invention amenable for use in in-situ PCR (polymerase chain reaction) which requires repeated cycles of higher and lower temperatures. A limitation of PCR. is the need to extract the target DNA or RNA prior to amplification that precludes correlation of the molecular results with the cytological or histological features of the sample. In situ PCR obviates that limitation by combining the cell localizing ability of ISH with the extreme sensitivity of PCR. The technique is described in U.S. Pat. No. 5,538,871 to Nuovo et al. which is incorporated herein.

Sections embedded in paraffin require as a first step deparaffinization of the embedded tissue. Using the thermal platform eliminates the use of harsh chemicals such as xylene, through the use of precisely controlled heating of individual slides allowing the paraffin embedded in the tissue to melt out and float in aqueous solution where it can be rinsed away. Paraffin, being less dense than water, once liquified rises through the aqueous buffer on the tissue sample and floats on top of this fluid. The liquid paraffin can then be removed from the microscope slide and away from the tissue sample by passing a fluid stream, either liquid or gaseous, over the liquid paraffin. Details of this procedure are set forth in U.S. patent application Ser. No. 60/099,018 filed Sep. 3, 1998 which is incorporated herein. A similar technique may be employed to remove embedding materials other than paraffin such as plastics although the addition of etching reagents may be required.

Heating the tissue with thermal platforms 50 in an appropriate aqueous solution has been found to improve the accessibility of the stain to the target molecule in the cell (protein, nucleic acid, carbohydrate, lipid, or small molecule). Lack of accessibility may be caused by cross-linking of the molecules by aldehydes used in preserving the tissue or by other changes in the confirmation caused by fixatives. Cross-linking of antigens causes a loss of antigenicity due to the chemical modification of antigenic proteins. This process of improving accessibility of the stain (biological or chemical) to the molecular target is referred to herein as "cell conditioning." For DNA targets the preferred conditioning solution is citrate buffer, the preferred temperature is up to about 95 degrees, and the preferred time of heating is about one hour. For protein targets the preferred conditioning solution is citrate buffer and the preferred temperature is up to about 100 degrees C. for about 42 minutes. Heating the tissue sample by the thermal platform decreases the degree of cross-linking in aldehyde treated tissue such that the modified antigen reverts to a form recognizable by a corresponding antibody thereby enhancing the staining. For RNA targets the preferred conditioning solution is citrate buffer and the preferred temperature is up to about 75 degrees C. for about one hour. Many alternatives to citrate buffer may be employed as cell conditioning solution. A list of such solutions appears in *Analytical Morphology*, Gu, ed., Eaton Publishing Co. (1997) at pp. 1-40. The solutions should generally have known molarity, pH, and composition. Sodium dodecyl sulfate (SDS), ethylene glycol are preferably added to the conditioning solution.

Typical In-Situ Hybridization (ISIT), In-Situ PCR, Immunohistochemical (IHC), Histochemical (HC), or Enzymehistochemical (EHC) methods as carried out with the apparatus of this invention includes the following steps.

1) Slides are prepared by applying a bar code to the slide indicating the In-Situ Hybridization, In-Situ PCR Immunohistochemical, Histochemical, or Enzymehistochemical process to be used with the sample.
2) Inserting a batch of slides in the apparatus, mounting each slide into a slide support.
3) Closing the apparatus and beginning the treatment process.
4) If the slides are to be deparaffinized in the apparatus as a pretreatment, each slide will be dry heated to temperatures above 60° C. Following the dry heat, the slides are washed with about 7 ml of DI water leaving a residual aqueous volume of about 300 µl. The slides are then covered with about 600 µl of evaporation inhibiting liquid. The slides remain at temperatures above 60° C. for an additional 6 minutes and are then rinsed again with about 7 ml DI water and covered with 600 µl of evaporation inhibiting liquid. The temperature of lowered to 37° C. The slides are deparaffinized and ready for the next phase of the indicated process.
5) Slides that are to be cell conditioned will be rinsed with about 7 ml DI water. A volume-reducing fixture within the apparatus will lower the residual volume from about 300111 to about 100 µl. Using a volume-adjusting fixture within the apparatus 2000 of cell conditioning solution will be added to the slide. The slide will then receive about 600111 of evaporation inhibiting liquid. The slide temperature will be raised to the assigned temperature in a range of 37° C. to 100° C., and fluid cycling will commence and be repeated every 6-8 minutes for a period of time up to 2 hours as set in the protocol. Slides are cooled to 37° C. and rinsed with ~7 ml of APK wash solution. At this point the slides are ready for the next phase of the indicated process.
6) As each slide pauses in the reagent application zone, the appropriate reagent vessel is moved by the reagent carousel to the reagent application station. A metered volume of reagent is applied to the slide. The reagent liquid passes through the evaporation inhibiting liquid layer to the underlying liquid layer.
7) The slide carousel then proceeds, moving slides directly in front of vortex mixing stations. The vortex mixer jets stir the reagents on the slide surface below the evaporation inhibiting liquid layer.
8a) For In-Situ Hybridization If process requires protein digestion, slides are rinsed with ~7 ml of APK. wash solution leaving a residual volume of 300 µL of buffer. The slide will then receive ~6001.tL of evaporation inhibiting liquid. Steps as described in steps 6 and 7 are repeated for digestive enzyme application. Selectable incubation times range from 2 min through to 32 minutes at 37° C. The slides are rinsed with ~7 mis of 2× SSC buffer, leaving a residual volume of 3004 of buffer. A volume reducing fixture is used to shift the volume from 3004 to ~1004. Steps as described in 6 and 7 are repeated for probe application. The slide will then receive 6004 of evaporation inhibiting liquid. Raise slide temperature to specified temperature in a range of 37° C. to 95° C. for denaturization or unfolding respectively of target and/or probe. Selectable incubation times range from 2 min through to 18 hrs. Rinsing occurs after hybridization employing user selectable stringency, which includes selectable salt concentrations of 2×, 1×, 0.5×, 0.1×SSC and temperature range 37° C. to 75° C. Following the probe step, the slides are washed with 1×APK wash buffer, and then receive 6004 of evaporation inhibiting liquid. Probes are detected directly as in the case of some labeled probes as in FISH, and indirectly for ISH using anti hapten antibody followed an appropriate detection technology.

If Clearing is desired, following the detection steps for the probe, slides will be rinsed with DI water and a detergent will be applied to clear the slides of the evaporation inhibiting liquid. Again the slides will be rinsed with DI water and the residual volume will be removed with the use of the volume reducing fixture. The slides will be dry heated at temperatures at or above 37° C. until all aqueous is evaporated from the tissue, cells or smears.

8b) For In-Situ PCR

If process requires protein digestion, slides are rinsed with ~7 ml of APK wash solution leaving a residual volume of 3004 of buffer. The slide will then receive ~6004 of evaporation inhibiting liquid. Steps as described in steps 6 and 7 are repeated for digestive enzyme application. Selectable incubation times range from 2 min through to 32 minutes at 37° C. The slides are rinsed with ~7 mls of DI Water, leaving a residual volume of ~3004 of buffer. A volume reducing fixture is used to shift the volume from 3004 to ~1004. Steps as described in step 7 are repeated for amplification reagent application. Amplification reagents are formulated for delivery to 1004 residual slide volume at temperatures at or above 37° C. The slide will then receive 6004 of evaporation inhibiting liquid. Raise slide temperature to specified temperature in a range of 37° C. to 95° C. for greater that 2 minutes to start PCR reaction. Heat cycling up to 30 cycles, will commence from 55° C. for 1.5 minutes to 89° C. for 45 seconds.

Following In-Situ PCR the slides will be subjected to In-Situ Hybridization as described in section 8c) For IHC, HC, EHC protocols, the slides are rinsed with ~7 mis of I×APK. wash or appropriate buffer, leaving a residual volume of 300

µL of buffer. A volume reducing fixture may or may not be used to shift the volume from 300 µL to 1000—The slide will then receive 600 µL of evaporation inhibiting liquid. Steps as described in step 7 are repeated for antibody or other reagent application.

Selectable incubation times range from 2 min through to 32 min.

Selectable incubation temperatures range from 37° C. to 95° C. depending on whether cell conditioning or deparaffinization is required.

Throughout the procedure, the slides are washed with 1×APK. wash or appropriate buffer, and then receive ~600 µL of evaporation inhibiting liquid. Proteins, carbohydrates, and enzymes are directly labeled, as in fluorescence, or indirectly using an appropriate detection technology. At the conclusion of the designated staining procedures, the slides are prepared for coverslipping with the automated clearing procedure, coverslipped, and reviewed microscopically for appropriate staining, be it DNA/RNA, protein, carbohydrate or enzyme.

The procedures set forth above, including sequence of steps, application of reagents, and temperature parameters above are preferably pre-programmed into the host computer by the manufacturer. Certain parameters, such as the reaction time, may optionally be modifiable by the user. Initial programming of the test is flexible enough to allow complex manipulation of the protocol and addition of multiple reagents (5-6 reagents) both before and after addition of the probe to the target tissue or specimen.

Within-run and between run temperature control is +1% of the target temperature and may be controlled as described previously. The operator may run multiple complex ISH protocols in the same run. This includes ability to program protocols for ISH methods that run at the same denaturation temperatures. Likewise, the system is accessible for slide temperature calibration by the operator without tedious dismantling of the instrument. The protocol changes for user-defined ISH protocols are protected by a security access. The system is barcode driven for both the slide and reagent system. There is also the option for operator manual control of all major hardware functions including reagent dispense, wash dispense, coverslip (high and low temperature) dispense, slide indexing and temperature control. This enables the user to help troubleshoot problems. User defined protocols allow the operator to control the temperature of all phases of the reaction except detection temperature. The software includes pre-programmed optimized protocols resident in the software to allow continuous introduction of the optimized turnkey probes.

EXAMPLES

The following non-limiting examples further illustrate and detail uses and applications of the invention disclosed herein.

Example I

Detection of High Risk Strains of Human Papaloma Virus (HPV) using Automated In-Situ Hybridization A cervical smear, collected by standard collection devices such as a cytobrush or by a ThinPrep™ slide method (Cytec, Inc.) which would normally be stained by the Papanicolau stain (Pap smear), is subjected to in situ hybridization with a probe set specific to High Risk HPV types. The specimen slide is loaded into the slide holder of the apparatus according to the present invention (hereinafter referred to as "staining apparatus"). The system is set to run the HPV in situ program. This program performs all the steps of the in situ reaction with no interaction required from the user once the program has been started.

The staining apparatus first performs Slide Pretreatment: at room temperature 1.×APK. (10×APK. Ventana P/N 250-042) rinse and Coverslip™ application, then a Protease digestion for 4 minutes at 37° C. with Protease 1 followed by a rinse step in 2×SSC. Following the 2×SSC rinse the residual slide volume is reduced from about 300 microliters to about 100 microliters and Coverslip™ is applied. The FITC-label DNA probe cocktail premixed with Hybridization Solution is applied to the slide from a Ventana definable dispenser. The specimen and the slide is heated to 72° C. for 4 minutes to denature both the probe and specimen DNA. The staining apparatus then ramps the temperature of the slide down to 37° C. and hybridization occurs for 2 hours at 37° C. The staining apparatus removes the probe mixture and Coverslip™ from the slide and performs the Post-Hybridization Washes. Post-Hybridization Wash solution (2×SSC) and Coverslips are added to the slide and the instrument heats the slide to 45° C. for 10 minutes. The staining apparatus removes the Post-Hybridization Wash solution and begins the Detection steps.

First, the staining apparatus rinses the slides with 1×APK and applies Coverslip. Then, an anti-FITC (serotec P/N MCA1320) antibody is applied from a dispenser to the slide and incubates the slide for 20 minutes while heating the slide to 37 degrees C. followed by APK rinse and Coverslip application. Then, a biotin labeled secondary antibody is added and incubated for 8 minutes at 37° C., also followed by an APK rinse and Coverslip application. A Streptavidin-Alkaline Phosphates conjugate is placed on the slide and staining apparatus incubates the slide for 30 minutes at 37 degrees C. After an APK rinse, Ventana Blue Detection Reagents are added to the slide and incubated for 20 minutes at room temperature. Ventana Blue Kit (P/N 760-060) comprises of Biotin labeled secondary antibody, Streptavidin-Alkaline Phosphatase and NBT/BCIP substrate. The slide is rinsed with DI Water, and the slide is heat dried by the instrument. At this Point, Nuclear Fast Red counterstain is applied to the slide, incubated for 5 minutes at room temperature, and the slide is rinsed with water.

Example II

Detection of mRNA of Epstien Barr Virus (EBER) in Paraffin Embedded Tissue Using Automated In-Situ Hybridization A 5 micron section was cut of spleen #EBV 37A and placed on a supper frost glass staining slide. The specimen slide was loaded into the slide holder of the apparatus according to the present invention (hereinafter referred to as "staining apparatus"). The staining apparatus was programmed to run the EBER in situ program. This program will perform all the steps of the in situ reaction with no interaction required from the user once the program has been started.

The staining apparatus first performs deparaffinization: slides were dry heated to 65° C. for 6 minutes, room temperature DI water rinses the slide, leaving 300 µL residual volume and 600 µL liquid coverslip, which prevents evaporation and protects the slide specimen from drying. The temperature remains at 65° C. to melt away the paraffin. Cell conditioning was done by rinsing the slide with DI water, then reducing the residual volume, and applying 2000, cell conditioning buffer (Citrate Buffer) and 60011L liquid Coverslip™. The slide was heated to 75° C. and the conditioning buffer and Coverslip™ were reapplied every 8 minutes for 40 minutes. The slide temperature was cooled to 37° C. and the slide was rinsed with room temperature 1×APK. Wash (Ventana 10×APK P/N 250-042) leaving 30011L residual slide volume and 6001.1L of liquid coverslip was applied. Protease digestion was for 8 minutes with Protease 1 (Ventana P/N 250-2018) at 37° C. Following digestion the slide was rinsed with room temperature 2× SSC (20×SSC Ventana P/N 650-012). Using a volume- reducing fixture in the staining apparatus the residual side volume was reduced from 300 μl to 1004, and 6004L of liquid coverslip was applied to the slide. The Dig-labeled (Boehringer Mannheim cat #1 417 231) oligonucleotide probe which was designed to target mRNA for EBER was premixed with Hybridization solution and the reagent was placed into a Ventana user defined dispenser(Ventana P/N 551-761). The probe was applied to the specimen and the slide was heated to 75° C. for 4 minutes to unwind the oligonucleotide and specimen mRNA. The staining apparatus then ramps to a temperature of the slide to 37° C., to hybridize for 2 hours. The staining apparaus removed the probe solution and Coverslip™ from the slide and performed 3 Post-Hybridization Washes. The Post Hybridization Washes consisted of washing the slide with 2× SSC at 42° C. for 4 minutes then washing the slide with 1×SSC at 42° C. for 4 minutes and finally 0.5×SSC 42° C. for 4 minutes. The staining apparatus then performed the detection steps. The slide was washed with 1×APK and coverslip was applied. An anti-Dig antibody (Sigma P/N D-8156) was applied to the slide and incubated for 16 minutes at 37° C. followed by 1×APK wash and Coverslip™ application. Then, a biotin labeled secondary antibody was added to the slide and incubated for 8 minutes at 37° C., followed by 1×APK wash and coverslip application. Following the secondary antibody, Streptavidin-Alkaline Phosphatase conjugate was applied and incubated for 30 minutes at 37° C. After an APK. wash and coverslip application Ventana Blue Detection Reagents were applied to the specimen and incubated for 20 minutes at 37° C. The slide was then washed with water and heat dried by the instrument. The biotin labeled secondary antibody, Streptavidin-Alkaline Phosphatase, and Detection Reagents are components of Ventana Blue Kit (Ventana PIN 760-060). Following dehydration of the specimen, the slide was covered with a glass coverslip and reviewed microscopically.

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

What is claimed is:

1. Apparatus for processing biological materials comprising:
    a fixed instrument platform;
    a rotating carousel including a plurality of thermal platforms mounted on the carousel each thermal platform including a heater and a temperature sensor;
    control electronics mounted on the carousel and electrically associated with the heater and the temperature sensor of each thermal platform, wherein the control electronics accept temperature set point information for each of the plurality of thermal platforms, monitors each temperature sensor and individually controls the heating of each heater associated with each of the plurality of thermal platforms mounted on the slide carousel; and
    a slip ring assembly mounted between the fixed instrument platform and the rotating carousel, the slip ring assembly including leads for transferring power from the fixed instrument platform to each of the heaters.

2. Apparatus for processing biological materials as claimed in claim 1 wherein the slip ring assembly includes brushes and slip rings.

3. Apparatus for processing biological materials comprising:
    a rotating carousel having a plurality of thermal platforms each thermal platform including a heater and a temperature sensor;
    control electronics mounted on the carousel, wherein the control electronics are in electrical communication with each temperature sensor and with each heater and wherein the control electronics accept temperature set point information about each thermal platform from a processor, monitors each of the temperature sensors and individually controls the heating of each of the heaters associated with each of the plurality of thermal platforms;
    a fixed instrument platform including the processor; and
    a slip ring assembly mounted between the fixed instrument platform and the rotating carousel the slip ring assembly including means for transferring power from the fixed instrument platform to the control electronics and for transferring temperature set point information from the processor to the control electronics.

4. Apparatus for processing biological materials as claimed in claim 3 wherein the slip ring assembly includes leads and wherein the leads are in communication with the control electronics.

5. Method for heating biological materials on individual slides in an apparatus comprising a rotating carousel having a plurality of thermal platforms each thermal platform including a heater and a temperature sensor, a processor located off of the rotating carousel, control electronics mounted on the rotating carousel the control electronics monitoring the temperature each temperature sensor and individually controlling the power directed to each of the plurality of heaters, and a slip ring assembly mounted between the rotating carousel and the fixed instrument platform for communicating electronic information from the processor to the control electronics, the method comprising the steps of:
    accessing information by the processor;
    converting the information into a serial communication format;
    sending the serial communication format information to the control electronics wherein the serial communication format information passes through the slip ring assembly; and
    controlling the temperature of the thermal platforms individually using the control electronics based on the serial communication information.

6. The method as claimed in claim 5 wherein the information accessed by the processor includes temperature setpoint information for each of the plurality of thermal platforms.

7. The method as claimed in claim 6 wherein controlling the thermal platforms temperature set point based on the serial communication information includes comparing the temperature setpoint information with temperature sensor information for a thermal platform and controlling the heating of the heater associated with the thermal platform based on the comparison of the temperature setpoint information with the temperature sensor information associated with the thermal platform.

8. The method as claimed in claim 5 wherein each of the plurality of thermal platforms support a slide, and wherein the step of sending the serial communication information to control electronics includes passing the serial communication through a slip ring of the slip ring assembly.

9. The method as claimed in claim 5 wherein the serial communication format is I²C (Inter Integrated Circuit) serial bus protocol.

10. Apparatus for processing biological materials comprising:
- a fixed instrument platform;
- a rotating carousel;
- a plurality of thermal platforms mounted on the rotating carousel each thermal platform including a device selected from the group consisting of a heater or a cooler;
- a temperature sensor associated with each thermal platform;
- a slip ring assembly mounted between the fixed instrument platform and the rotating carousel, the slip ring assembly including leads for transferring power from the fixed instrument platform to the device selected from the group consisting of the heater or the cooler of each of the plurality of thermal platforms mounted on the slide carousel; and
- a microprocessor mounted on the rotating carousel for monitoring each temperature sensor the microprocessor individually controlling the temperature of each of the plurality of thermal platforms mounted on the slide carousel by controlling power to the device selected from the group consisting of the heater or the cooler.

11. Apparatus for processing biological materials comprising:
- a housing including a lower section associated with an upper section the lower section including a rotating slide carousel;
- a plurality of thermal platforms mounted on the rotating slide carousel each thermal platform including a device selected from the group consisting of a heater and a cooler;
- a sensor associated with each thermal platform for detecting the temperature of the thermal platform;
- a slip ring assembly between the housing and the rotating carousel that allows the rotating carousel to rotate relative to the housing, the slip ring assembly including leads for transferring power from the housing to each of the plurality of thermal platforms mounted on the slide carousel; and
- control electronics mounted on the carousel for monitoring the sensors and for controlling the temperature of each of the plurality of thermal platforms mounted on the slide carousel by controlling power to the device selected from the group consisting of the heater and the cooler.

* * * * *